US011033693B2

(12) United States Patent
Li et al.

(10) Patent No.: US 11,033,693 B2
(45) Date of Patent: Jun. 15, 2021

(54) MEDICATION DISPENSER

(71) Applicant: Jabil Circuit (Shanghai) Ltd., Shanghai (CN)

(72) Inventors: Ying Li, Shanghai (CN); Ying-Zhen Tong, Shanghai (CN); Yi-Nong Zhao, Shanghai (CN); Fang-Long Xu, Shanghai (CN); Yong-Feng Song, Shanghai (CN); Conor Mulcahy, Shanghai (CN); Xiao Qiang Fei, Shanghai (CN)

(73) Assignee: Jabil Circuit (Shanghai) Co., Ltd., Shanghai (CN)

(*) Notice: Subject to any disclaimer, the term of this patent is extended or adjusted under 35 U.S.C. 154(b) by 0 days.

(21) Appl. No.: 16/445,833

(22) Filed: Jun. 19, 2019

(65) Prior Publication Data

US 2019/0298946 A1    Oct. 3, 2019

Related U.S. Application Data

(63) Continuation of application No. 15/722,713, filed on Oct. 2, 2017, now Pat. No. 10,369,305.

(30) Foreign Application Priority Data

Oct. 3, 2016  (CN) .......................... 201610876992.3

(51) Int. Cl.
*A61M 15/00*    (2006.01)
*A61M 11/00*    (2006.01)

(52) U.S. Cl.
CPC ...... *A61M 15/0065* (2013.01); *A61M 11/001* (2014.02); *A61M 15/00* (2013.01);
(Continued)

(58) Field of Classification Search
CPC .......... A61M 15/0045; A61M 15/0003; A61M 15/00043; A61M 15/0051;
(Continued)

(56) References Cited

U.S. PATENT DOCUMENTS 3,092,576 A * 6/1963 Daubman ................. B04B 7/06
                                                    210/146
5,020,527 A   6/1991 Dessertine
(Continued)

FOREIGN PATENT DOCUMENTS

CN         1668354 A      9/2005
CN       204043730 U     12/2014
(Continued)

OTHER PUBLICATIONS

Search Report appended to an Office Action issued to Chinese counterpart application No. 201610876992.3 by the CNIPA dated Mar. 11, 2020, with an English translation thereof.
(Continued)

*Primary Examiner* — Rakesh Kumar
(74) *Attorney, Agent, or Firm* — Young Basile Hanlon & MacFarlane, P.C.

(57) ABSTRACT

A medication dispenser includes a base seat, a circuitry unit and an outer casing. The base seat includes a mouthpiece. The circuitry unit includes a first circuit board, a battery, and first and second switches disposed on the first circuit board. The outer casing is movable relative to the base seat between a close position where the outer casing covers the mouthpiece and where the first switch is actuated such that electric power is prevented from being supplied from the battery to the first circuit board, and an open position where the outer casing uncovers the mouthpiece and where the second switch is actuated such that electric power is supplied from the battery to the first circuit board.

18 Claims, 26 Drawing Sheets

(52) U.S. Cl.
CPC ...... *A61M 15/008* (2014.02); *A61M 15/0045*
(2013.01); *A61M 15/0046* (2014.02); ***A61M
15/0051*** (2014.02); A61M 15/0021 (2014.02);
A61M 15/0063 (2014.02)

(58) Field of Classification Search
CPC .......... A61M 15/0068; A61M 15/0065; A61M
15/0046; A61M 15/008; A61M 15/00;
A61M 15/0021; A61M 15/0063; A61M
11/001
USPC ............ 128/203.15, 203.21, 200.14, 203.25;
221/27, 225, 72, 70, 69, 71
See application file for complete search history.

(56) References Cited

U.S. PATENT DOCUMENTS

| | | | |
|---|---|---|---|
| 5,207,217 A | 5/1993 | Cocozza et al. | |
| 5,450,054 A * | 9/1995 | Schmersal | F16H 59/044 338/128 |
| 5,860,419 A * | 1/1999 | Davies | A61M 15/0051 128/203.15 |
| 5,873,360 A * | 2/1999 | Davies | A61M 15/0051 128/203.15 |
| 6,012,454 A | 1/2000 | Hodson et al. | |
| 6,026,809 A | 2/2000 | Abrams et al. | |
| 6,029,659 A | 2/2000 | O'Connor | |
| 6,104,592 A * | 8/2000 | Pohl | H01H 71/04 324/207.15 |
| 6,234,167 B1 | 5/2001 | Cox et al. | |
| 6,684,880 B2 | 2/2004 | Trueba | |
| 6,971,383 B2 | 12/2005 | Hickey et al. | |
| 7,198,044 B2 | 4/2007 | Trueba | |
| 7,249,687 B2 * | 7/2007 | Anderson | A61M 15/0045 128/203.15 |
| 7,434,579 B2 | 10/2008 | Young et al. | |
| 7,896,192 B2 * | 3/2011 | Conley | G07F 17/0092 221/15 |
| 7,950,389 B2 | 5/2011 | Eason et al. | |
| 8,584,673 B2 | 11/2013 | Thoemmes et al. | |
| 8,967,508 B2 * | 3/2015 | Kindelan | A47J 19/06 241/34 |
| 9,636,471 B2 | 5/2017 | Anderson et al. | |
| 9,980,880 B1 * | 5/2018 | Litton | G07F 17/0092 |
| 10,300,227 B2 | 5/2019 | Sutherland et al. | |
| 10,369,305 B2 * | 8/2019 | Li | A61M 15/0046 |
| 10,528,074 B1 * | 1/2020 | Olsson | G05G 9/047 |
| 2002/0053344 A1 | 5/2002 | Davies et al. | |
| 2002/0066451 A1 | 6/2002 | Davies et al. | |
| 2004/0025877 A1 | 2/2004 | Crowder et al. | |
| 2007/0062525 A1 * | 3/2007 | Bonney | A61M 15/0051 128/203.21 |
| 2007/0199951 A1 * | 8/2007 | Levasseur | G07F 11/24 221/124 |
| 2007/0215149 A1 | 9/2007 | King et al. | |
| 2008/0054745 A1 * | 3/2008 | Sentmanat | H02K 21/12 310/89 |
| 2008/0193617 A1 * | 8/2008 | Sus | B65B 43/305 426/438 |
| 2009/0315306 A1 | 12/2009 | Worrell et al. | |
| 2010/0137802 A1 * | 6/2010 | Yodfat | A61M 5/1452 604/152 |
| 2011/0025437 A1 * | 2/2011 | Preaux | F21V 23/0414 335/207 |
| 2011/0041845 A1 * | 2/2011 | Solomon | A61M 15/009 128/203.12 |
| 2011/0232584 A1 * | 9/2011 | Valencia | A01K 27/009 119/719 |
| 2012/0037157 A1 | 2/2012 | Rohrschneider et al. | |
| 2013/0153696 A1 * | 6/2013 | Kindelan | A47J 19/06 241/36 |
| 2013/0310729 A1 * | 11/2013 | White | G01R 19/145 604/20 |
| 2014/0158704 A1 | 6/2014 | Anderson et al. | |
| 2015/0027286 A1 * | 1/2015 | Yuyama | B65D 83/04 83/105 |
| 2015/0338445 A1 * | 11/2015 | White | A61N 1/18 604/20 |
| 2016/0107820 A1 * | 4/2016 | Macvittie | B65D 83/0454 221/13 |
| 2017/0239415 A1 * | 8/2017 | Hwang | G06F 19/00 |
| 2017/0264991 A1 * | 9/2017 | Horst | H02J 7/0045 |
| 2018/0296767 A1 * | 10/2018 | Sall | A61M 5/31568 |
| 2018/0335159 A1 * | 11/2018 | Rogers | F16K 17/363 |
| 2019/0022339 A1 * | 1/2019 | Richardson | B65D 83/386 |
| 2019/0201293 A1 * | 7/2019 | Brady | A61J 7/0445 |

FOREIGN PATENT DOCUMENTS

| | | |
|---|---|---|
| WO | 9949920 A1 | 10/1999 |
| WO | 0303515 A1 | 5/2003 |
| WO | 03090825 A1 | 11/2003 |
| WO | 03092576 A2 | 11/2003 |
| WO | 2005009325 A2 | 2/2005 |
| WO | 2005080001 A1 | 9/2005 |
| WO | 2011129791 A1 | 10/2011 |
| WO | 2011129793 A1 | 10/2011 |
| WO | 2017037161 A1 | 3/2017 |

OTHER PUBLICATIONS

Search Report appended to an Office Action, which was issued to Chinese counterpart application No. 201811141317.1 by the CNIPA dated Feb. 26, 2021 with an English translation thereof.

* cited by examiner

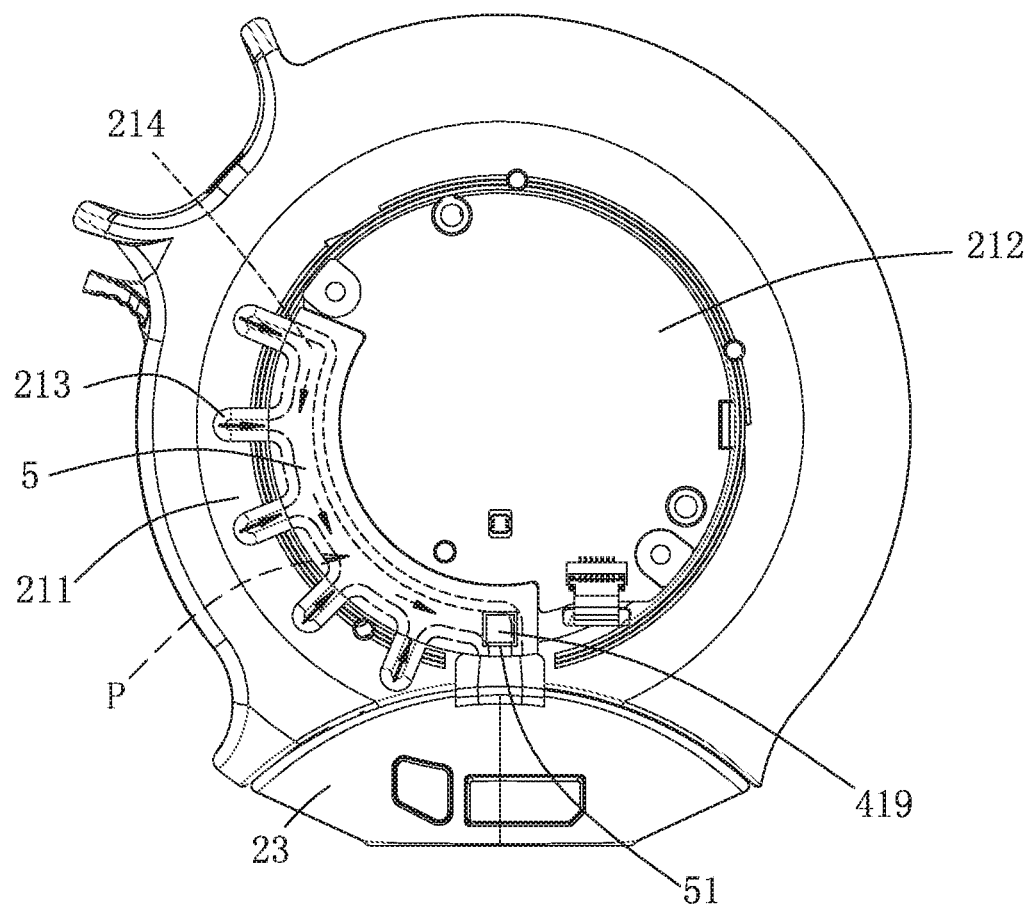
F I G. 10

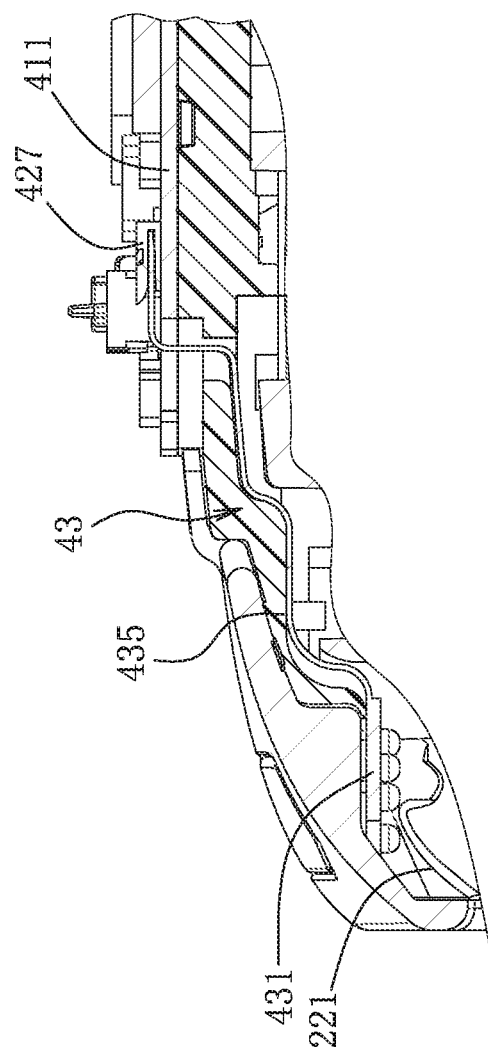
F I G. 11

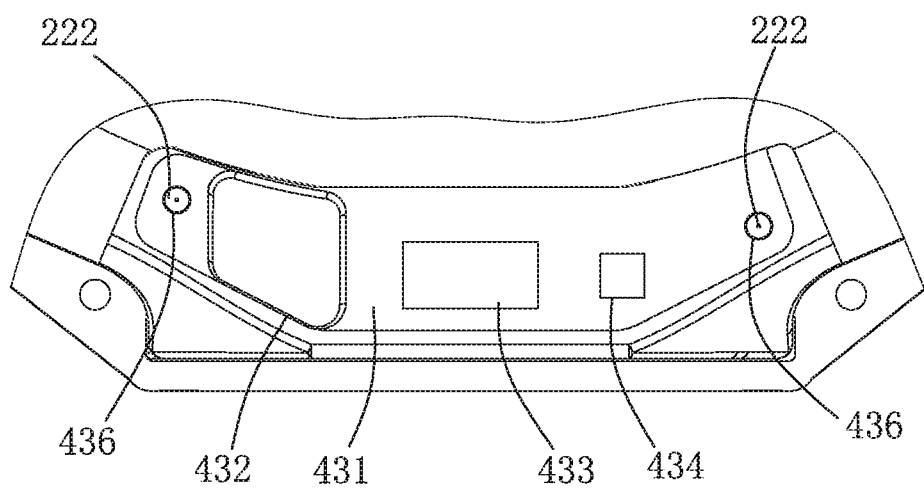
F I G. 12

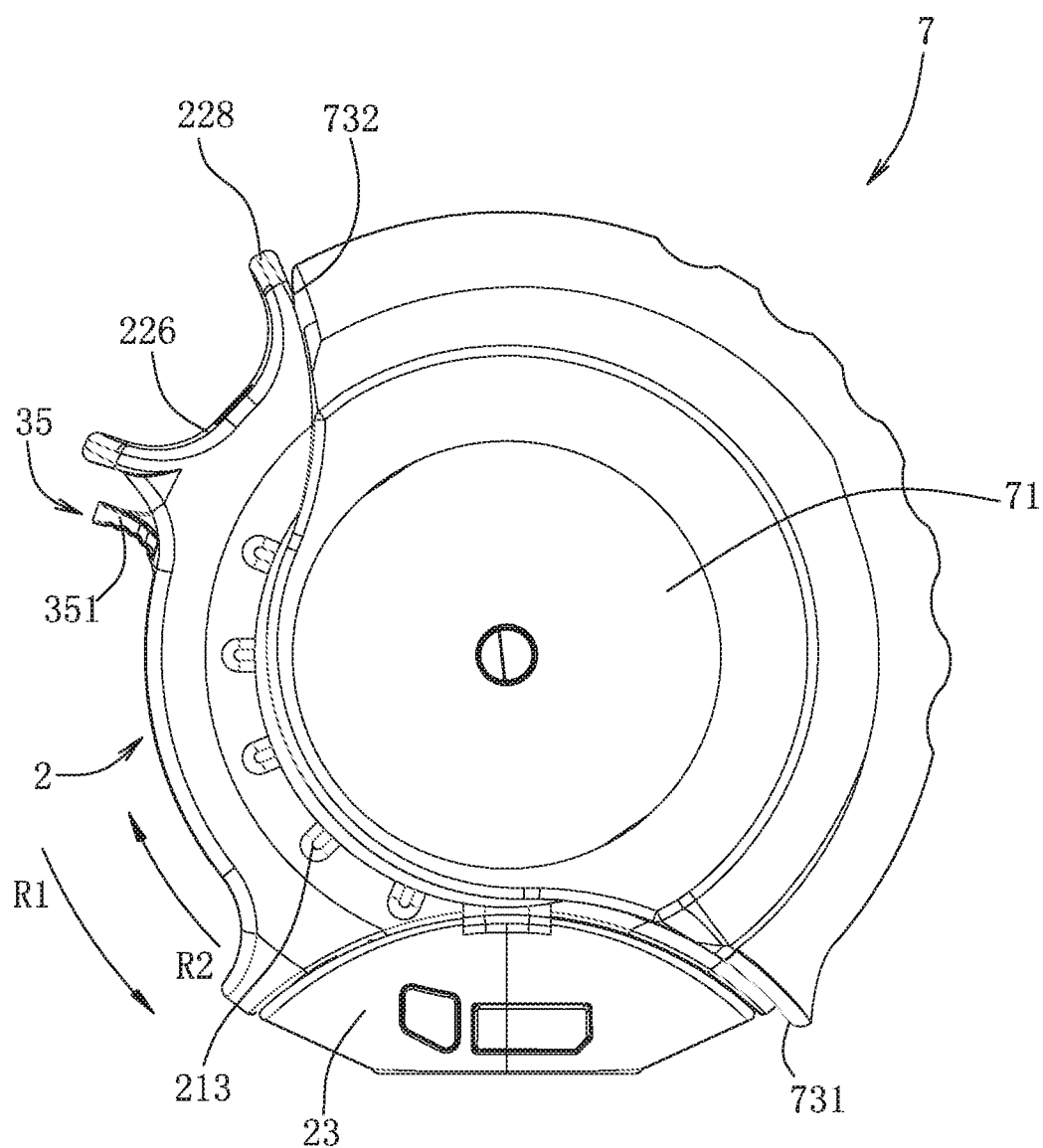
F I G. 15

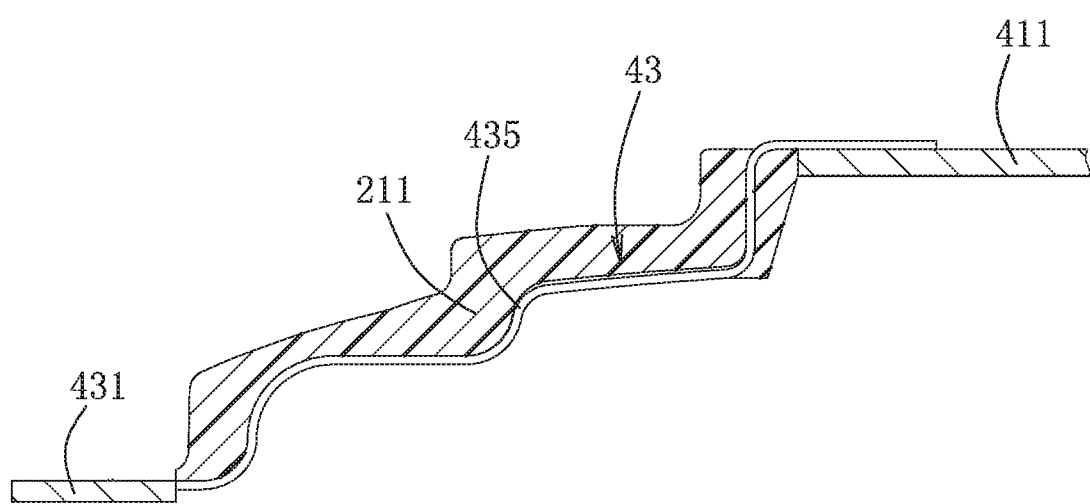
F I G. 23

MEDICATION DISPENSER

CROSS-REFERENCE TO RELATED APPLICATIONS

This application is a continuation application (CA) of co-pending U.S. patent application Ser. No. 15/722,713, filed on Oct. 2, 2017, which claims priority of Chinese Patent Application No. 201610876992.3, filed on Oct. 3, 2016, which are both incorporated by reference herein.

FIELD

The disclosure relates to a medication dispenser, and more particularly to a medical inhaler.

BACKGROUND

A conventional medication dispenser includes a mouthpiece, a conveying strip that has a plurality of capsules each containing a dose of medication, and a lever that is associated with the conveying strip. Upon operation of the lever, the capsules are aligned with the mouthpiece one at a time, so a user is able to inhale the dose in an aligned one of the capsules via the mouthpiece.

SUMMARY

The object of the disclosure is to provide a medication dispenser that can switch between an idle/standby state and an operating state.

According to the disclosure, the medication dispenser includes a base seat, a circuitry unit and an outer casing. The base seat includes a mouthpiece. The circuitry unit is disposed on the base seat, and includes a first circuit board, a battery, a first switch that is disposed on the first circuit board, and a second switch that is disposed on the first circuit board. The outer casing is movably mounted to the base seat, and is movable relative to the base seat between a close position where the outer casing covers the mouthpiece, and an open position where the outer casing uncovers the mouthpiece. When the outer casing is at the close position, the first switch is actuated such that electric power is prevented from being supplied from the battery to the first circuit board. When the outer casing is at the open position, the second switch is actuated such that electric power is supplied from the battery to the first circuit board.

BRIEF DESCRIPTION OF THE DRAWINGS

Other features and advantages of the disclosure will become apparent in the following detailed description of the embodiments with reference to the accompanying drawings, of which:

FIG. 10 is a schematic top view illustrating a flow path formed in the first embodiment;

FIG. 11 is a fragmentary sectional view taken along line S2-S2 in FIG. 5;

FIG. 12 is a schematic fragmentary top view illustrating a capacitive sensor, an infrared proximity sensor and an infrared temperature sensor of the first embodiment;

FIG. 15 is a schematic top view illustrating the outer casing at an open position;

FIG. 23 is a fragmentary sectional view illustrating a second embodiment of the medication dispenser according to the disclosure;

DETAILED DESCRIPTION

Figure 1:
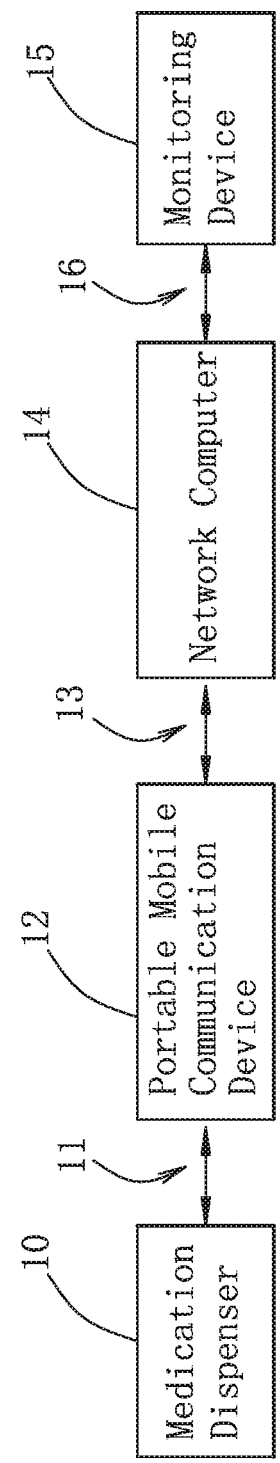
FIG. 1 is a block diagram illustrating a first embodiment of the medication dispenser according to the disclosure used in a medical care monitoring system.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, the first embodiment of the medication dispenser 10 according to the disclosure is for use in a medical care monitoring system. The medication dispenser 10 can be connected to a portable mobile communication device 12 via a first communication network 11 to enable data transfer therebetween. By such, a patient can be conveniently informed about the method of operation and the status of the medication dispenser 10 by the portable mobile communication device 12. The portable mobile communication device 12 may be configured as a smartphone, a smartwatch or a notebook computer. The portable mobile communication device 12 can be connected to a network computer 14 via a second communication network 13 to enable data transfer from the portable mobile communication device 12 to the network computer 14. By such, physicians or pharmacists can monitor the status of the medication treatment of the patient by a monitoring device 15 that is connected to the network computer 14 via a third communication network 16. The monitoring device 15 may be configured as a desktop computer or a smartphone. The first communication network 11 may be a Bluetooth network. Each of the second and third communication networks 13, 16 may be the Internet. In one embodiment, the first communication network 11 is a Bluetooth Low Energy (BLE) network.

Figure 2:
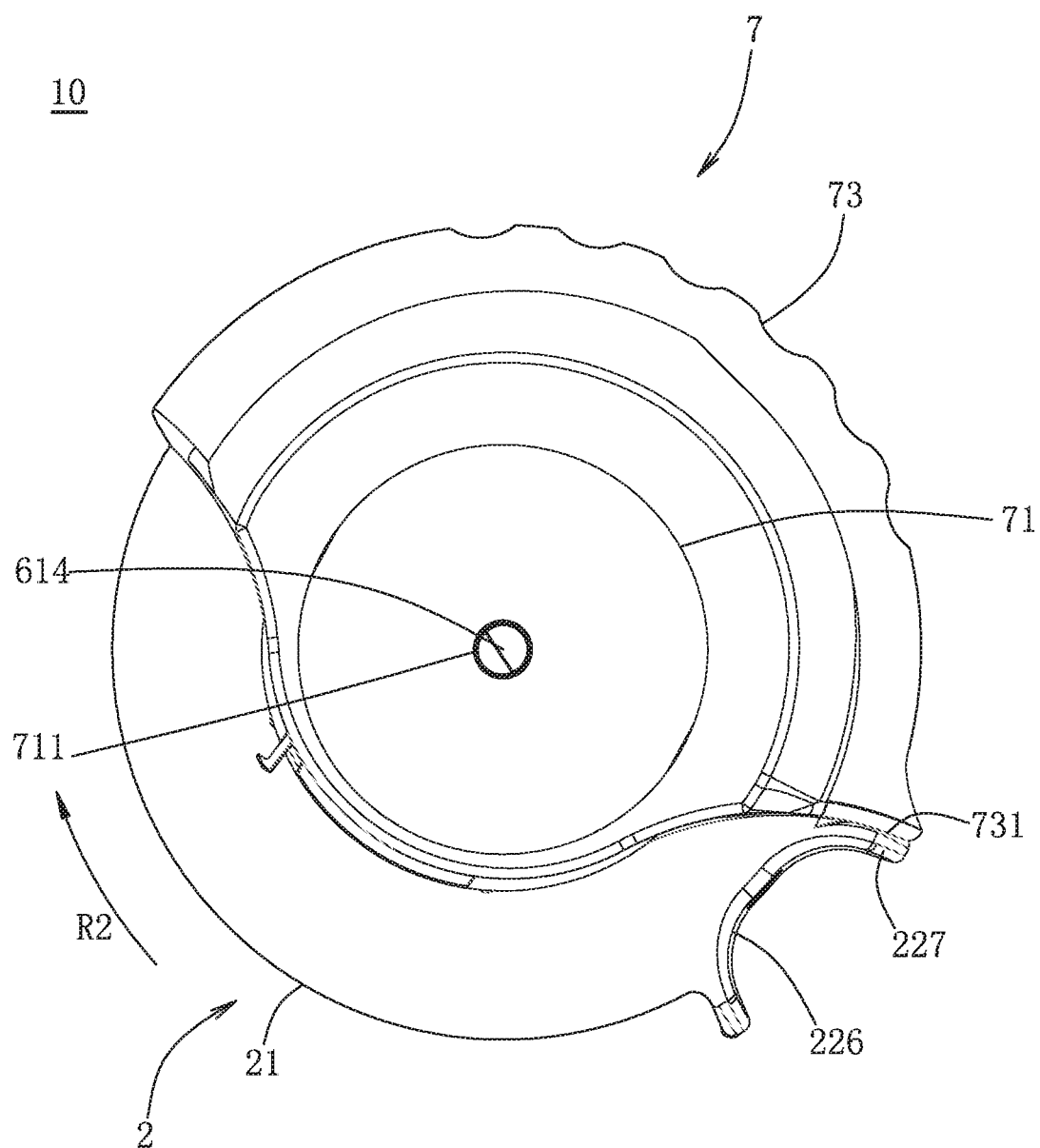
FIG. 2 is a schematic top view illustrating an outer casing of the first embodiment at a close position.
Figure 3:
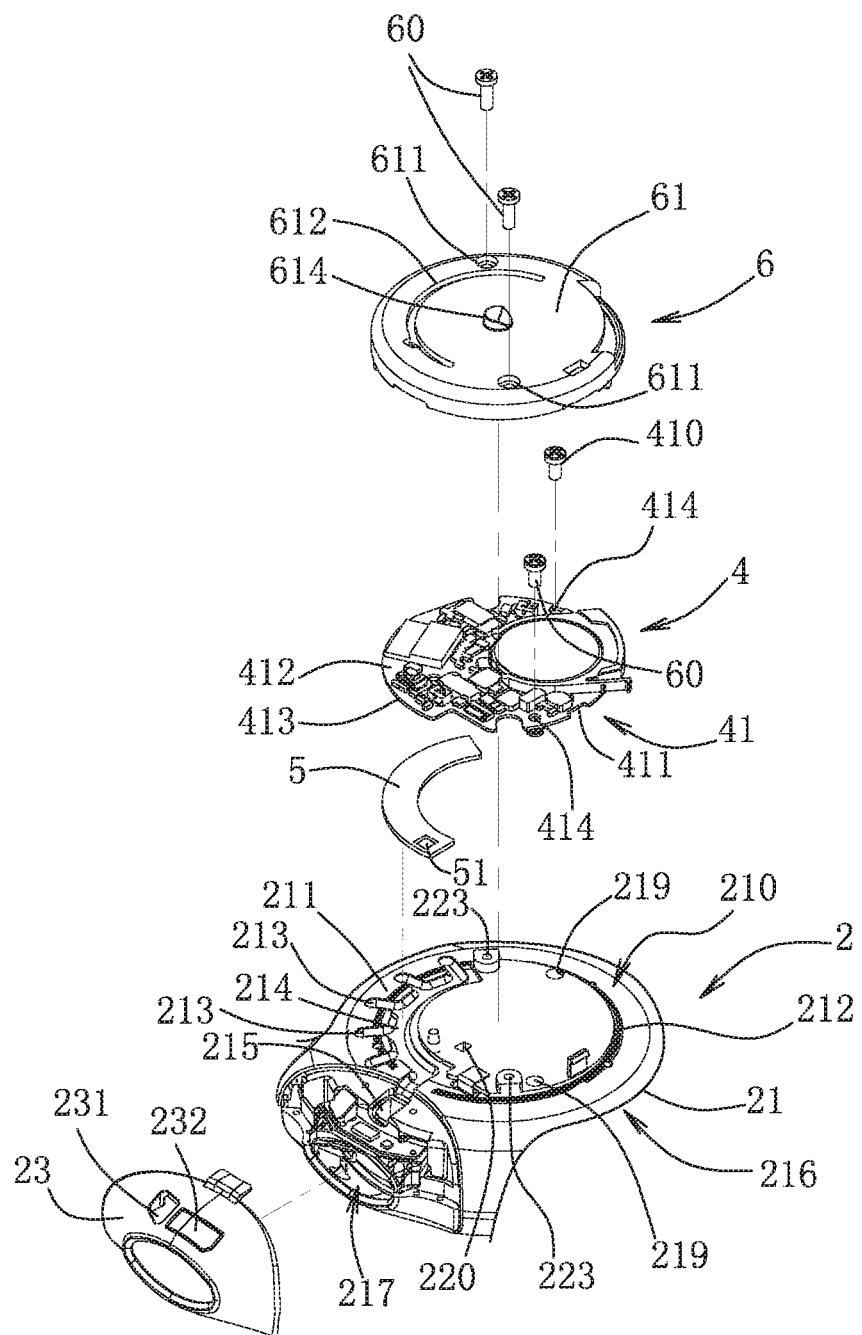
FIG. 3 is fragmentary exploded perspective view illustrating the first embodiment.
Figure 4:
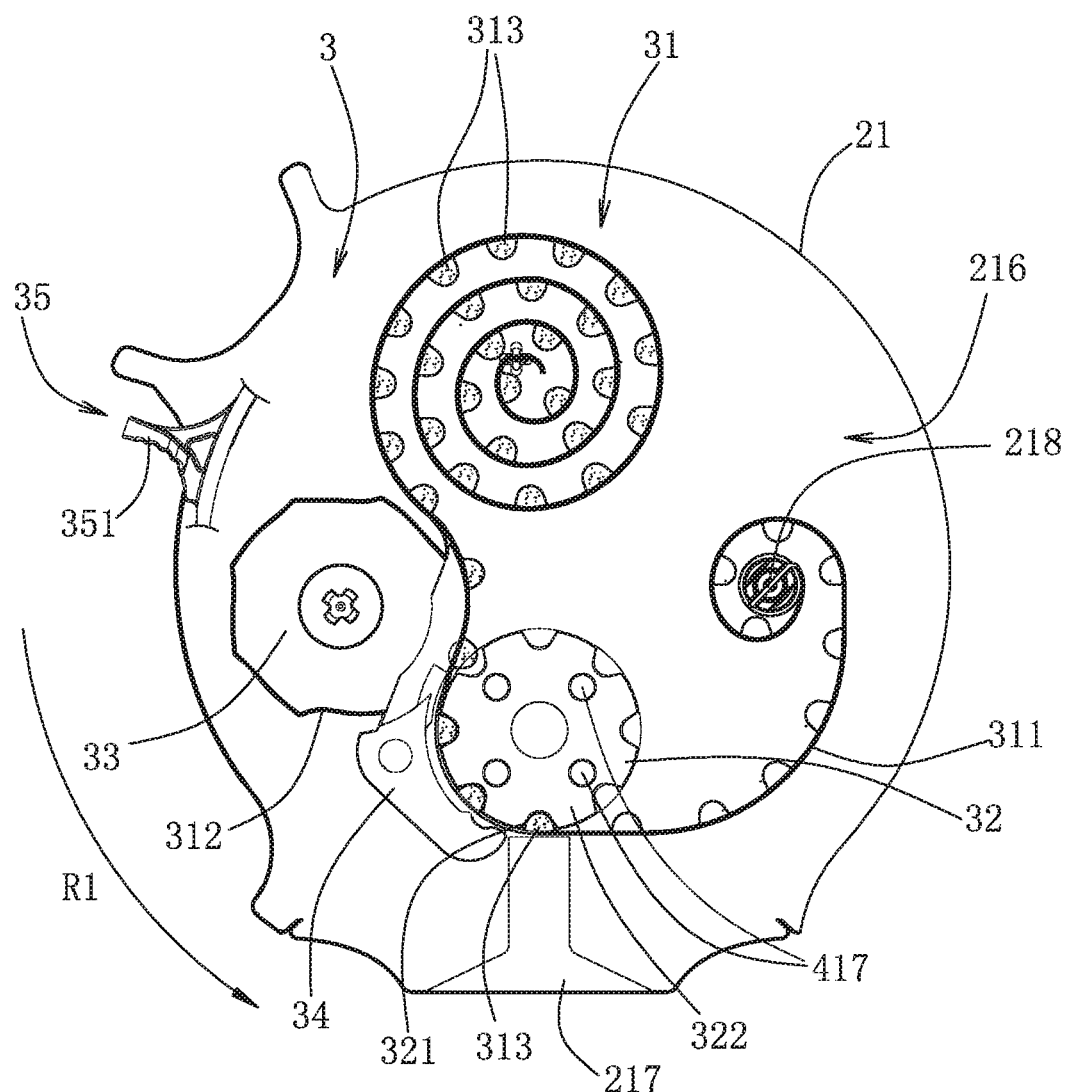
FIG. 4 is schematic top view illustrating a dispensing device of the first embodiment.

Referring to FIGS. 2 to 4, the first embodiment of the medication dispenser 10 is configured as a medical inhaler, and includes a base seat 2, a dispensing device 3, a circuitry unit 4, a seal member 5, a cover unit 6 and an outer casing 7.

The base seat 2 includes a seat body 21, and a mouthpiece 23 that is mounted to the seat body 21. The seat body 21 has a top wall 210. The top wall 210 has a main wall portion 211, and a protruding wall portion 212 that protrudes upwardly from the main wall portion 211. The main wall portion 211 of the top wall 210 is formed with a plurality of spaced-apart intake channels 213, and an arc-shaped communicating channel 214 that is in fluid communication with the intake channels 213. The seat body 21 defines a retaining space 216 that is for retaining the dispensing device 3, an inlet path 215 that is in fluid communication with an end of the communicating channel 214 and the retaining space 216, and an outlet path 217 that is in fluid communication with the retaining space 216 and that is located below the inlet path 215. The mouthpiece 23 covers the inlet path 215 and the outlet path 217, and is for contact with the patient's lips.

The dispensing device 3 includes a conveying strip 31, a notched wheel 32, a wrapping wheel 33, a peeler 34 and an operating member 35. The conveying strip 31 includes a base sheet 311 and a lid sheet 312. The base sheet 311 of the conveying strip 31 is elongated and has a longitudinal end connected to a post 218 of the seat body 21. The base sheet 311 extends around the notched wheel 32, and has a plurality of spaced-apart capsules 313 each of which contains a dose of powdered medication. The lid sheet 312 of the conveying strip 31 is elongated, and is for sealing the capsules 313. A portion of the lid sheet 312 is separated from the base sheet 311, and is wound around the wrapping wheel 33. The notched wheel 32 is rotatably mounted to the seat body 21, and has a plurality of equidistantly and angularly spaced-apart notches 321 that are formed in an outer surrounding surface thereof. Each of the notches 321 is for receiving one of the capsules 313 therein, so that the conveying strip 31 meshes with the notched wheel 32. The wrapping wheel 33 is rotatably mounted to the seat body 21, and wraps the portion of the lid sheet 312 that is separated from the base sheet 311.

The wrapping wheel 33 and the notched wheel 32 are associated with each other by two gears (not shown) that are respectively connected to the wrapping wheel 33 and the notched wheel 32 and that mesh with each other. The peeler 34 is disposed between the notched wheel 32 and the wrapping wheel 33, and is for separating the lid sheet 312 from the base sheet 311. The operating member 35 has a major portion mounted in the receiving space 216. The operating member 35 is associated with the notched wheel 32 by virtue of a one-way transmission mechanism (not shown), and has a lever portion 351 that projects out of the seat body 21. Upon depression of the lever portion 351, the operating member 35 drives the notched wheel 32 to rotate by a predetermined angle via the one-way transmission mechanism, so that one of the capsules 313 of the conveying strip 31 is driven to be aligned with and in fluid communication with the inlet path 215 and the outlet path 217, so as to permit the patient to inhale the dose therein via the mouthpiece 23. At the same time, the peeler 34 partially separates the lid sheet 312 from the base sheet 311, and the wrapping wheel 33 is driven by the notched wheel 32 to wrap the separated portion of the lid sheet 312. In this embodiment, the intake channels 213 cooperate with the communicating channel 214, the inlet path 215, the notch 321 of the notched wheel 32 that is aligned with the inlet path 215, and the outlet path 217 to define a flow path (P, see FIGS. 6 and 10). The dispensing device 3 is known in the art, and is not limited to that disclosed above.

Figure 5:
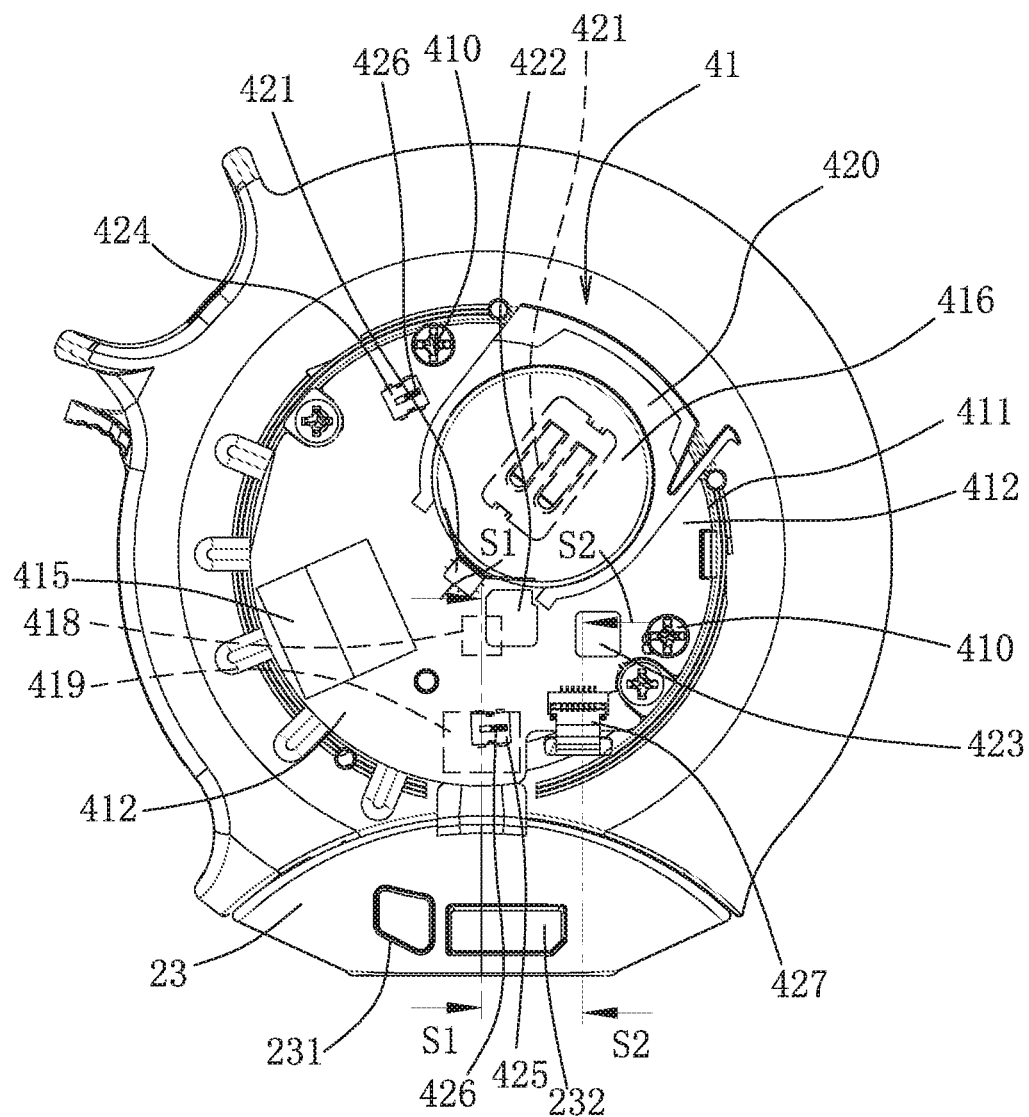
FIG. 5 is a schematic top view illustrating a main circuit module of the first embodiment.

Referring to FIGS. 3 to 5, the circuitry unit 4 includes a main circuit module 41. The main circuit module 41 includes a first circuit board 411. The first circuit board 411 has a top surface 412, a bottom surface 413, and two spaced-apart through holes 414 each of which is formed through the top and bottom surfaces 412, 413. The first circuit board 411 is fixedly mounted on the protruding wall portion 212 of the top wall 210 of the seat body 21 by two screws 410, each of which extends through a respective one of the through holes 414 of the first circuit board 411 and threadedly engages a respective one of two threaded holes 219 formed in the protruding wall portion 212 of the top wall 210. A portion of the bottom surface 413 of the first circuit board 411 corresponds in position to the communicating channel 214 and is located above the communicating channel 214.

Figure 6:
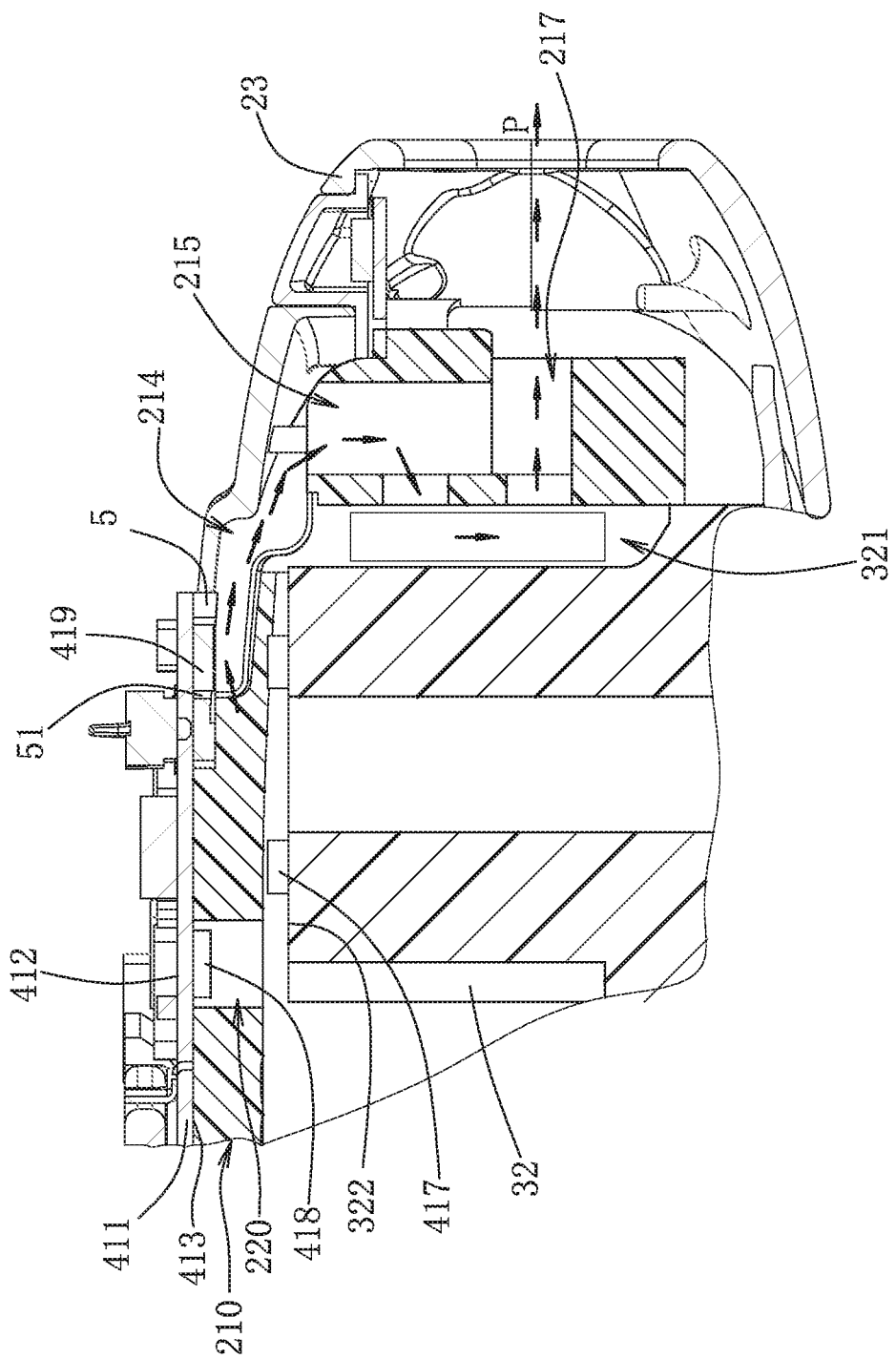
FIG. 6 is a fragmentary sectional view taken along line S1-S1 in FIG. 5.

Referring to FIGS. 4 to 6, the main circuit module 41 further includes a chip 415, a battery 416, a plurality of magnets 417, a Hall sensor 418 and a pressure sensor 419. The chip 415 is mounted to the top surface 412 of the first circuit board 411. In one embodiment, the chip 415 is configured as a Bluetooth Low Energy System on Chip (BLE SoC), and has relatively low power consumption and manufacturing cost. The first communication network 11 (see FIG. 1) between the chip 415 and the portable mobile communication device 12 (see FIG. 1) adopts Bluetooth wireless communication. The battery 416 is removably mounted to a positioning frame 420 that is disposed on the top surface 412 of the first circuit board 411. The battery 416 is electrically coupled to the first circuit board 411 by two conductive plates 421 (see FIG. 5) for providing electric power to the first circuit board 411.

The magnets 417 are fixedly mounted to a top surface 322 of the notched wheel 32, and are equidistantly and angularly spaced apart from each other. The number of the notches 321 of the notched wheel 32 is even. The number of the magnets 417 is even, and is half the number of the notches 321. Only one of any two adjacent ones of the notches 321 is radially aligned with a corresponding one of the magnets 417 with respect to a center of the notched wheel 32. In one embodiment, the number of the notches 321 is eight, and the number of the magnets 417 is four. The notched wheel 32 is rotated by 360 degrees by depressing the lever portion 351 of the operating member 35 eight times.

Figure 7:
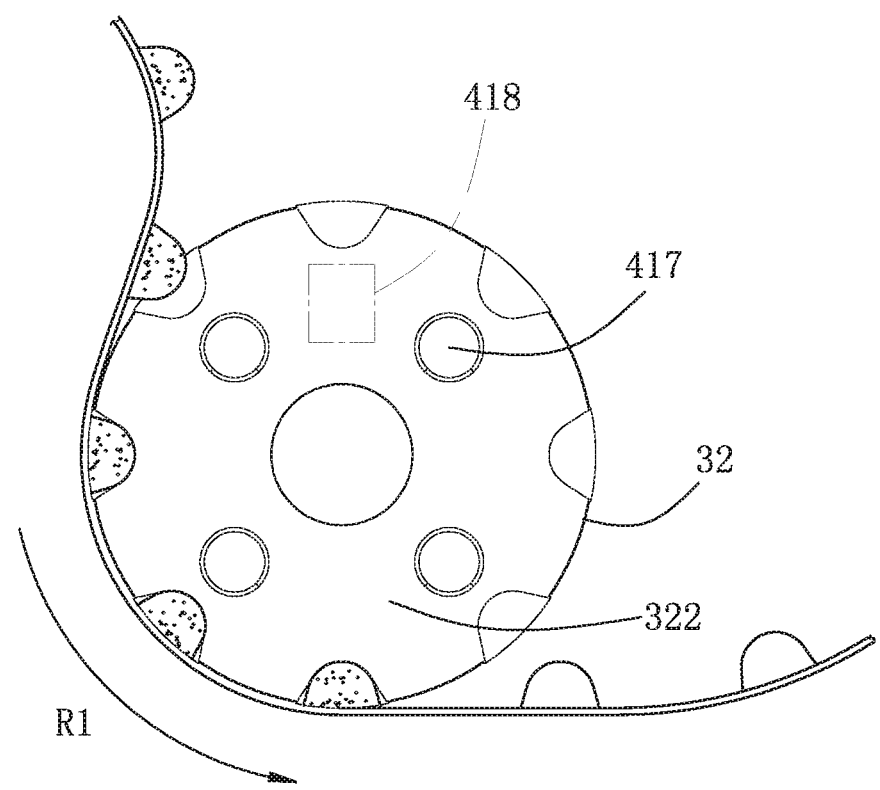
FIG. 7 is a schematic top view illustrating a Hall sensor of the first embodiment in a first detecting state.
Figure 8:
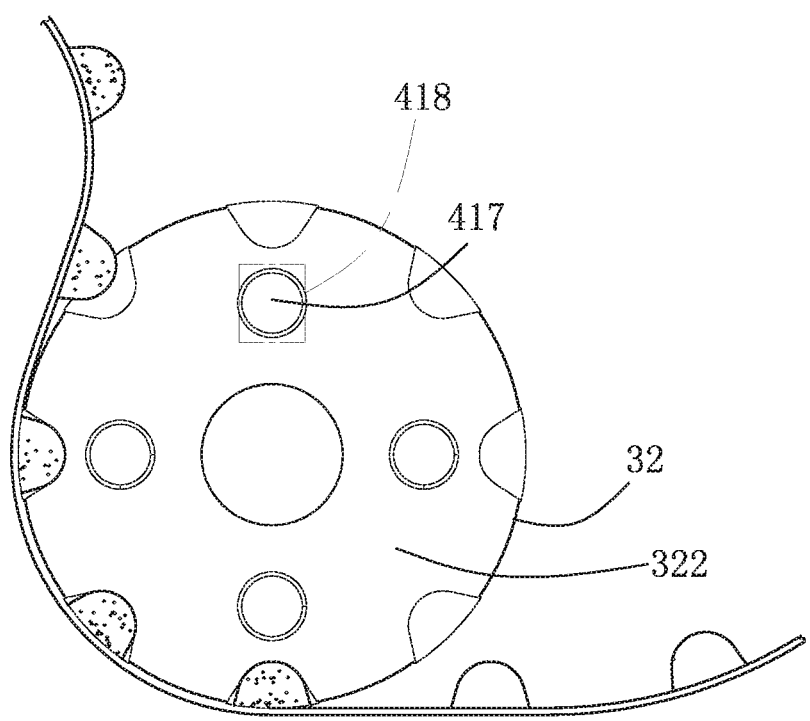
FIG. 8 is another schematic top view illustrating the Hall sensor in a second detecting state.
Figure 9:
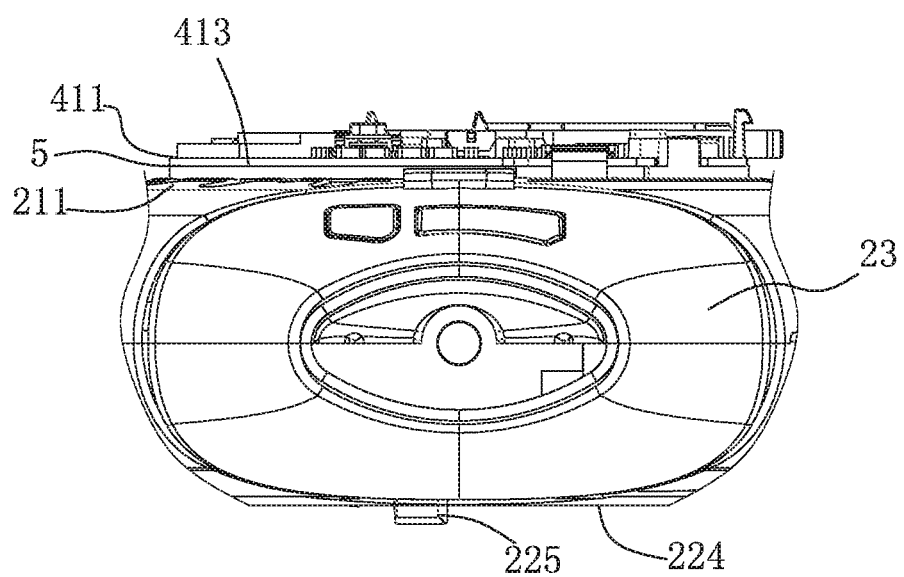
FIG. 9 is a schematic side view illustrating the first embodiment.

Referring to FIGS. 6 to 8, the Hall sensor 418 is disposed on the bottom surface 413 of the first circuit board 411. More specifically, the Hall sensor 418 is located within a mount hole 220 formed in the top wall 210 of the seat body 21, and is located above and spaced part from the top surface 322 of the notched wheel 32. When the notched wheel 32 is at the position shown in FIG. 7, the Hall sensor 418 is not registered with the magnets 417, and is in a first detecting state. When the notched wheel 32 is rotated in a first rotational direction (R1) to the position shown in FIG. 8 upon depression of the lever portion 351 of the operating member 35, the Hall sensor 418 is registered with one of the magnets 417, and is in a second detecting state. The Hall sensor 418 generates a signal during the switch from the first detecting state to the second detecting state or from the second detecting state to the first detecting state upon each depression of the operating member 35. The chip 415 (see FIG. 5) receives the signal generated by the Hall sensor 418 to determine a decrement of the number of the remaining doses by one upon each depression of the operating member 35. In addition, the chip 415 transfers the number of times of the depression of the operating member 35 to the portable mobile communication device 12 via the first communication network 11 (see FIG. 1), so the patient can be informed of the number of the remaining doses by the portable mobile communication device 12.

Referring to FIGS. 3, 6, 9, and 10, the seal member 5 may be made of silicone. The seal member 5 has opposite top and bottom surfaces respectively abutting against the bottom surface 413 of the first circuit board 411 and the main wall portion 211 of the top wall 210 of the seat body 21. The seal member 5 seals a top opening of the communicating channel 214, so the air flowing into the communicating channel 214 via the intake channels 213 all flows into the inlet path 215. The pressure sensor 419 is disposed on the bottom surface 413 of the first circuit board 411, and is disposed adjacent to the communicating channel 214 for detecting the pressure difference in the communicating channel 214 during the inhalation of the patient.

In one embodiment, the seal member 5 is formed with an installation space 51 that is located at an end portion of the communicating channel 214 proximate to the inlet path 215. The pressure sensor 419 is disposed on the bottom surface 413 of the first circuit board 411, and is mounted to the installation space 51 of the seal member 5. Since the pressure sensor 419 is disposed adjacent to the end portion of the communicating channel 214 proximate to the inlet path 215 at which the velocity of air flow is relatively high, the accuracy of the pressure difference determined by the pressure sensor 419 is enhanced. Moreover, since each of the capsules 313 of the conveying strip 31 is located downstream of the pressure sensor 419 during the inhalation of the patient when it is in spatial communication with the inlet path 215 and the outlet path 217, the powdered medication in the capsules 313 does not get in contact with the pressure sensor 419 to thereby prevent break down of the pressure sensor 419.

In one embodiment, the Hagen-Poiseuille law is adopted to determine whether the flow rate of the inhalation of the patient is sufficient to deliver the dose. At least a portion of the communicating channel 214 is assumed to be a uniform straight tube. The airflow is assumed to be a laminar flow and the air is regarded as an incompressible fluid.

$$\Delta P = \frac{128\mu L Q}{\pi d^4}$$

Where:
ΔP denotes the pressure difference between two ends of the tube;
μ denotes the dynamic viscosity;
L denotes the length of the tube;
Q denotes the volumetric flow rate; and
d denotes the diameter of the tube.

Referring to FIGS. 1 and 5, the main circuit module 41 further includes an inertial measurement unit 422, an environmental sensor 423, a first switch 424 and a second switch 425. The inertial measurement unit 422, the environmental sensor 423, the first switch 424 and the second switch 425 are disposed on the top surface 412 of the first circuit board 411. In one embodiment, the inertial measurement unit 422 is configured as a 6-axis inertial measurement unit, and is for detecting the tilt angle of the medication dispenser 10. The chip 415 receives the information detected by the inertial measurement unit 422, and transfers the information about the tilt angle of the medication dispenser 10 to the portable mobile communication device 12 via the first communication network 11. The portable mobile communication device 12 displays the tilt angle of the medication dispenser 10 via an application installed in the portable mobile communication device 12, and the patient can be informed of the tilt angle of the medication dispenser 10 by the portable mobile communication device 12. In one embodiment, when the tile angle of the medication dispenser 10 is greater than 15 degrees, the portable mobile communication device 12 would warn the patient that the dose in the notch 321 (see FIG. 6) that is aligned with the inlet and outlet paths 215, 217 may leak out, and orientation of the medication dispenser 10 needs to be adjusted. In one embodiment, the inertial measurement unit 422 also detects the acceleration of the medication dispenser 10 during vibration or impact of the medication dispenser 10, and the portable mobile communication device 12 then displays the status of the medication dispenser 10.

The environmental sensor 423 detects the humidity and temperature during use, load or transport of the medication dispenser 10. The chip 415 receives the information detected by the environmental sensor 423, and transfers the information about the humidity and temperature to the portable mobile communication device 12 via the first communication network 11. The portable mobile communication device 12 displays the humidity and temperature via an application, and the patient can be informed of the environmental humidity and temperature by the portable mobile communication device 12. When the environmental humidity or temperature of the medication dispenser 10 exceeds a predetermined value, the portable mobile communication device 12 would warn the patient that the medication dispenser 10 is in an unfavorable environmental condition, and that the patient may stop taking the medication in the medication dispenser 10.

The first switch 424 and the second switch 425 are spaced apart from each other. Each of the first and second switches 424, 425 includes a push arm 426. When the push arm 426 of the first switch 424 is actuated, electric power is prevented from being supplied to the first circuit board 411 from the battery 416, so the medication dispenser 10 is switched into an idle/standby state. When the push arm 426 of the second switch 425 is actuated, electric power is supplied to the first circuit board 411 from the battery 416, so the medication dispenser 10 is switched into an operating state.

Referring to FIGS. 5, 11 and 12, the circuitry unit 4 further includes a lip detection module 43. The lip detection module 43 includes a second circuit board 431, a capacitive sensor 432, an infrared proximity sensor 433, an infrared temperature sensor 434 and a communication sub-unit 435. The second circuit board 431 is a stiff board, and is formed with two positioning holes 436 (see FIG. 12). A surrounding wall 221 of the seat body 21 that defines the outlet path 217 is formed with two positioning protrusions 222. The positioning protrusions 222 respectively engage the positioning holes 436 of the second circuit board 431, so the second circuit board 431 is fixedly mounted on a top surface of the surrounding wall 221. The capacitive sensor 432, the infrared proximity sensor 433 and the infrared temperature sensor 434 are disposed on the second circuit board 431. The infrared proximity sensor 433 is located between the capacitive sensor 432 and the infrared temperature sensor 434. The capacitive sensor 432 is exposed from an opening 231 formed in the mouthpiece 23 for contact with the patient's lips. The mouthpiece 23 has a shield portion 232. The shield portion 232 is made of light-transmissible material, and covers the infrared proximity sensor 433 and the infrared temperature sensor 434. In one embodiment, the communication sub-unit 435 is configured as a flexible circuit board. The communication sub-unit 435 is substantially disposed in the seat body 21, and has an end extending out of the seat body 21 and electrically coupled to an electric connector 427 that is disposed on the top surface 412 of the first circuit board 411, and an opposite end extending out of the seat body 21 and electrically coupled to the second circuit board 431. By such, the second circuit board 431 is electrically coupled to the first circuit board 411 via the communication sub-unit 435.

When the patient places the mouthpiece 23 onto his mouth, the infrared proximity sensor 433 first detects the approach of the patient's lips, the capacitive sensor 432 then detects the contact of the patient's lips therewith, and the infrared temperature sensor 434 finally detects the temperature of the patient's lips. Each of the capacitive sensor 432, the infrared proximity sensor 433 and the infrared temperature sensor 434 generates a signal upon detection of the presence of the patient's lips. The chip 415 determines that the patient is using the medication dispenser 10 upon reception of all of the signals generated by the capacitive sensor 432, the infrared proximity sensor 433 and the infrared temperature sensor 434 via the second circuit board 431, the communication sub-unit 435 and the first circuit board 411. By virtue of the capacitive sensor 432, the infrared proximity sensor 433 and the infrared temperature sensor 434, the chip 415 is able to more accurately determine if the patient is using the medication dispenser 10. For example, the medication dispenser 10 is not considered to be in use when the chip 415 receives only one or two of the signals generated by the capacitive sensor 432, the infrared proximity sensor 433 and the infrared temperature sensor 434.

Figure 13:
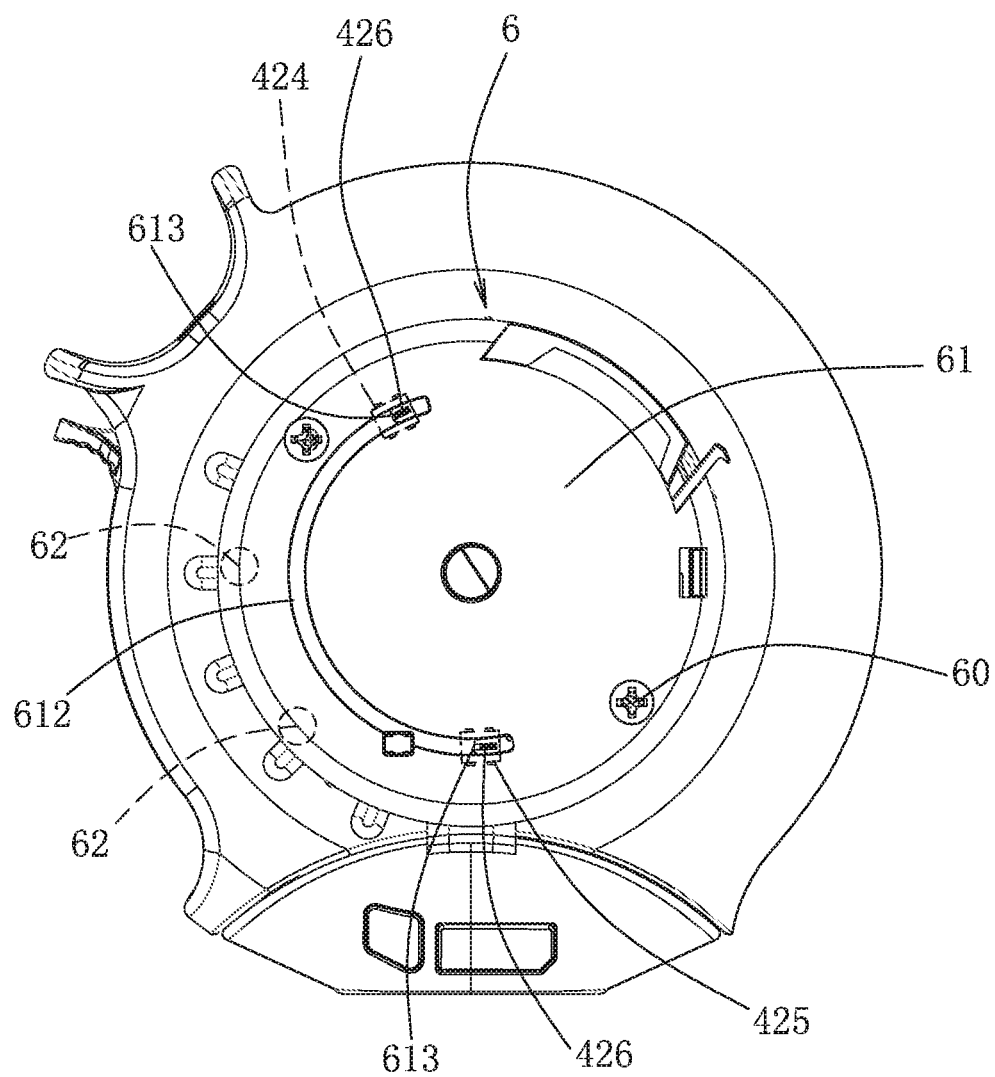
FIG. 13 is a schematic top view illustrating a cover unit of the first embodiment.

Referring to FIGS. 3 and 13, the cover unit 6 covers the main circuit module 41, and includes a cover plate 61. Two screws 60 respectively extend through two through holes 611 formed in the cover plate 61, and respectively and threadedly engage two threaded holes 223 formed in the protruding wall portion 212 of the top wall 210 of the seat body 21, so that the cover plate 61 is fixedly mounted to the top wall 210. The cover plate 61 has two protruding blocks 62 formed on a bottom surface thereof and corresponding in position to the seal member 5. The protruding blocks 62 abut against the top surface 412 of the first circuit board 411, and press the first circuit board 411 against the seal member 5 so as to establish an air-tight seal between the seal member 5 and the top wall 210 of the seat body 21.

The cover plate 61 further has an arc-shaped guide groove 612 that is formed in a top surface of the cover plate 61, and two communication holes 613 that are formed in the bottom surface of the cover plate 61 and that are respectively in spatial communication with two opposite ends of the guide groove 612. The push arm 426 of each of the first and second switches 424, 425 extends into the guide groove 612 via a respective one of the communication holes 613.

Referring to FIGS. 2, 3, 13, 14 and 16, the outer casing 7 has an upper plate 71, a lower plate (not shown) that is spaced apart from the upper plate 71 and that is disposed below the upper plate 71, an arc-shaped side plate 73 (see FIG. 2) that is connected between the upper plate 71 and the lower plate, and a slide block 74. The upper plate 71 is formed with a pivot hole 711 (see FIG. 2). The cover plate 61 further has a pivot axle 614 that is pivoted to the pivot hole 711 of the upper plate 71. The lower plate of the outer casing 7 is formed with a pivot hole (not shown). The seat body 21 further has a pivot axle 225 (see FIG. 9) that is formed on a bottom wall 224 thereof and that is pivoted to the pivoted hole of the lower plate of the outer casing 7. By such, the outer casing 7 is rotatable relative to the base seat 2 and the cover unit 6 between a close position (see FIG. 2) and an open position (see FIG. 15). The slide block 74 has a base portion 741 (see FIG. 14) fixedly mounted to an inner surface of the upper plate 71, and a protruding portion 742 protruding downwardly from the base portion 741. The protruding portion 742 of the slide block 74 extends into the guide groove 612 of the cover plate 61 for contact with the push arm 426 of the first switch 424 or with the push arm 426 of the second switch 425.

Figure 14:
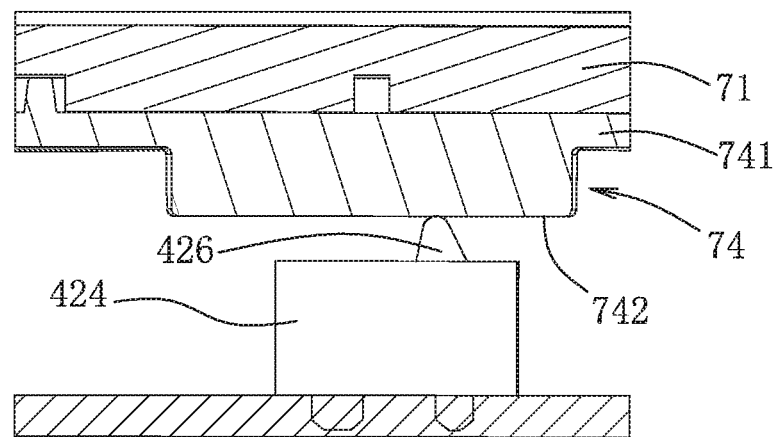
FIG. 14 is a fragmentary sectional view illustrating the outer casing in contact with a first switch.

The operation of the medication dispenser 10 is described as follows:

Referring to FIGS. 2, 5 and 14, when the outer casing 7 is at the close position, the mouth piece 23, the intake channels 213 and lever portion 351 of the operating member 35 are covered by the outer casing 7, and a first end 731 of the side plate 73 of the outer casing 7 abuts against a first flange 227 of a thumb hold portion 226 of the seat body 21. The protruding portion 742 of the slide block 74 actuates the push arm 426 of the first switch 424, so electric power is not supplied to the first circuit board 411 from the battery 416, and the medication dispenser 10 is in the idle/standby state.

Figure 16:
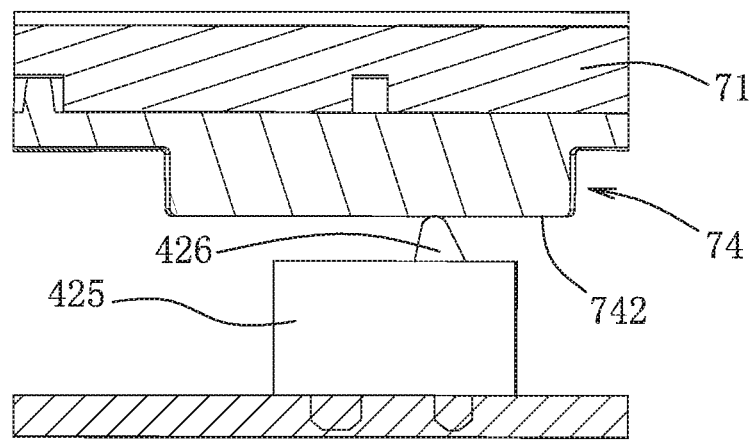
FIG. 16 is a fragmentary sectional view illustrating the outer casing in contact with a second switch.

Referring to FIGS. 5, 15 and 16, the patient can hold the upper plate 71 and the lower plate of the outer casing 7 by one hand, and insert the thumb of the other hand into the thumb hold portion 226 of the seat body 21 to rotate the base seat 2 in a second rotational direction (R2, see FIG. 2) relative to the outer casing 7 until the outer casing 7 is moved to the open position (see FIG. 15). During the movement of the outer casing 7 from the close position to the open position, the protruding portion 742 of the slide block 74 is first separated from the push arm 426 of the first switch 424, and then actuates the push arm 426 of the second switch 425, so electric power is permitted to be supplied to the first circuit board 411 from the battery 416, and the medication dispenser 10 is switched into the operating state. The chip 415 of the medication dispenser 10 is automatically paired with the portable mobile communication device 12 via the first communication network 11.

When a second end 732 of the side plate 73 of the outer casing 7 abuts against a second flange 228 of the thumb hold portion 226 of the seat body 21 of the base seat 2, the relative rotation between the base seat 2 and the outer casing 7 is stopped, and the outer casing 7 is moved to the open position such that the mouthpiece 23, the intake channels 213 and the lever portion 351 of the operating member 35 are uncovered.

Figure 17:
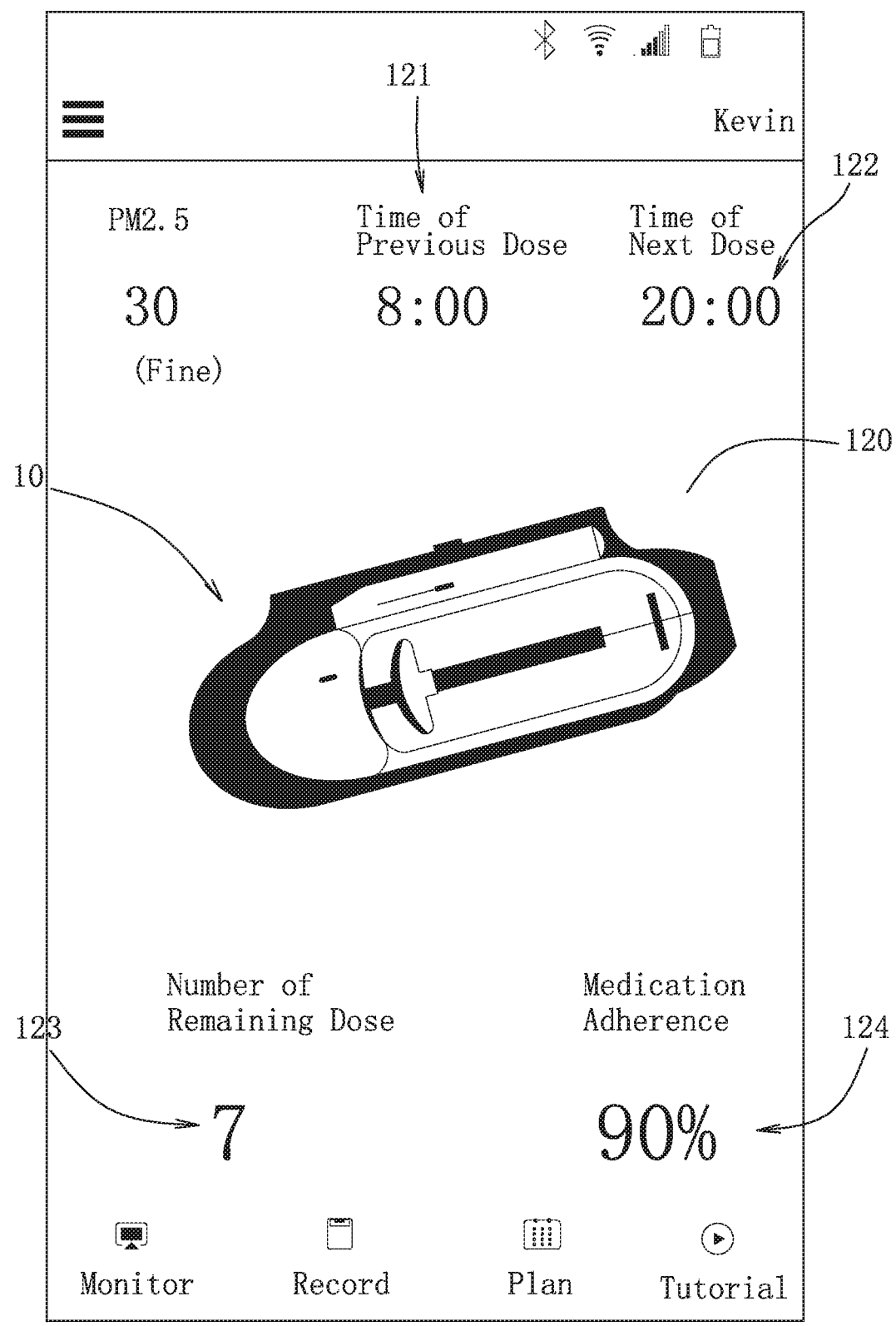
FIGS. 17-22 illustrate a display of a portable mobile communication device executing an application.

Referring to FIG. 17, after the medication dispenser 10 is switched to the operating state and is paired with the portable mobile communication device 12, the patient can operate the portable mobile communication device 12 to execute the application. In response, the application controls the portable mobile communication device 12 to display in an animation display area 120, a time-of-previous-dose display area 121 located above the animation display area 120, a time-of-next-dose display area 122 located at a lateral side of the time-of-previous-dose display area 121, a number-of-remaining-dose display area 123 located below the animation display area 120, and a medication adherence display area 124 located at a lateral side of the number-of-remaining-dose display area 123. The animation display area 120 first displays an animation or a video of the medication dispenser 10 to remind the patient that the next step is to depress the lever portion 351 of the operating member 35.

Referring to FIGS. 4, 5, 7 and 8, when the notched wheel 32 is rotated in the first rotational direction (R1) upon the depression of the operating member 35 to align the next capsule 313 with the mouthpiece 23, the Hall sensor 418 generates the signal during the switch between the first detecting state and the second detecting state. The chip 415 receives the signal generated by the Hall sensor 418 to determine a decrement of the number of the remaining doses by one, and records that the signal generated by the Hall sensor 418 is received once.

Figure 18:
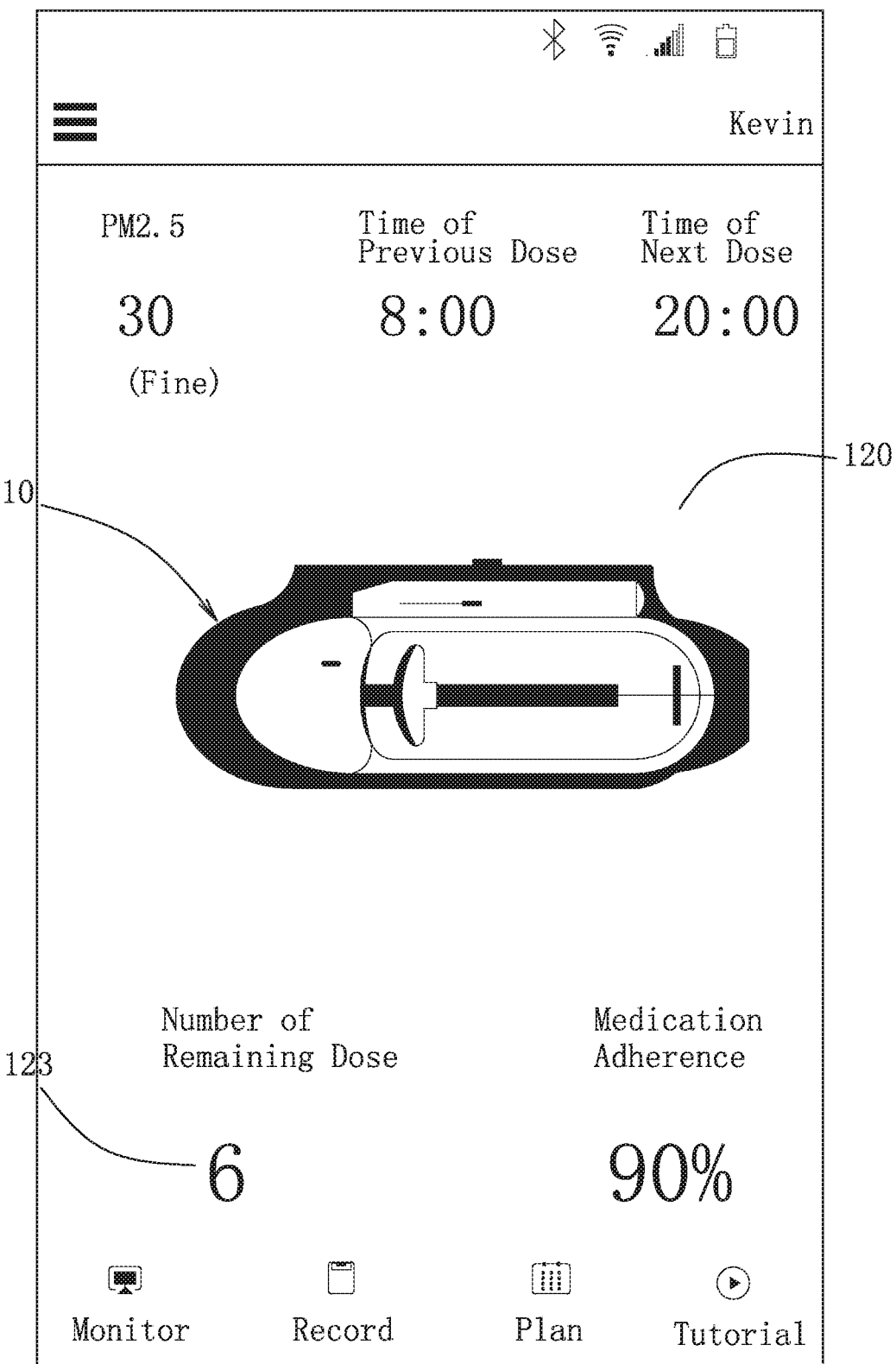

Referring to FIG. 18, the animation display area 120 then displays an image or a video of the medication dispenser 10 being disposed horizontally in order to remind the patient to keep the medication dispenser 10 horizontal for preventing leakage of the dose in the capsule 313 aligned with the mouthpiece 23 (see FIG. 6).

Figure 19:
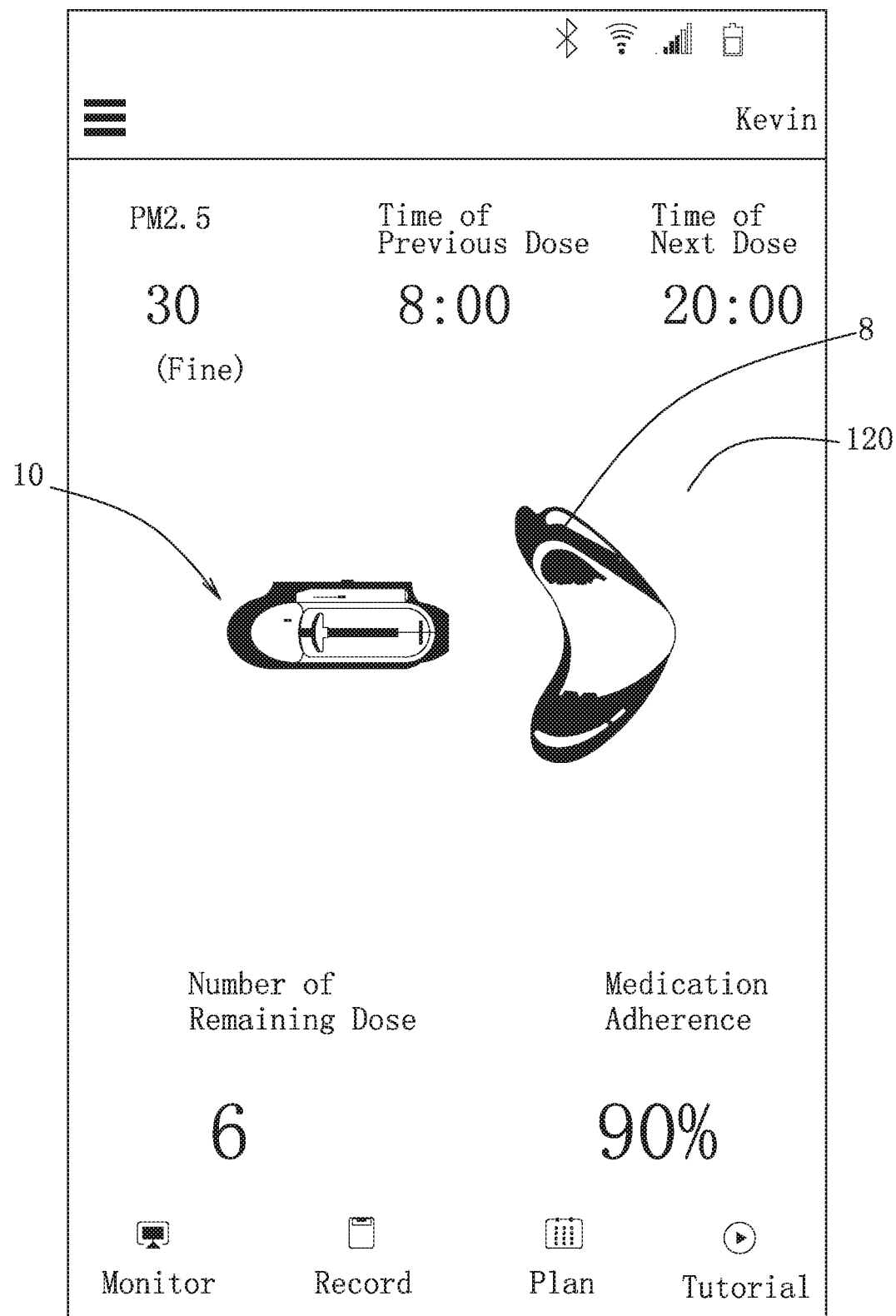

Referring to FIG. 19, afterward, the animation display area 120 displays an image or a video of the medication dispenser 10 and a mouth in order to remind the patient to place the mouthpiece 23 (see FIG. 3) of the medication dispenser 10 onto his mouth.

Figure 20:
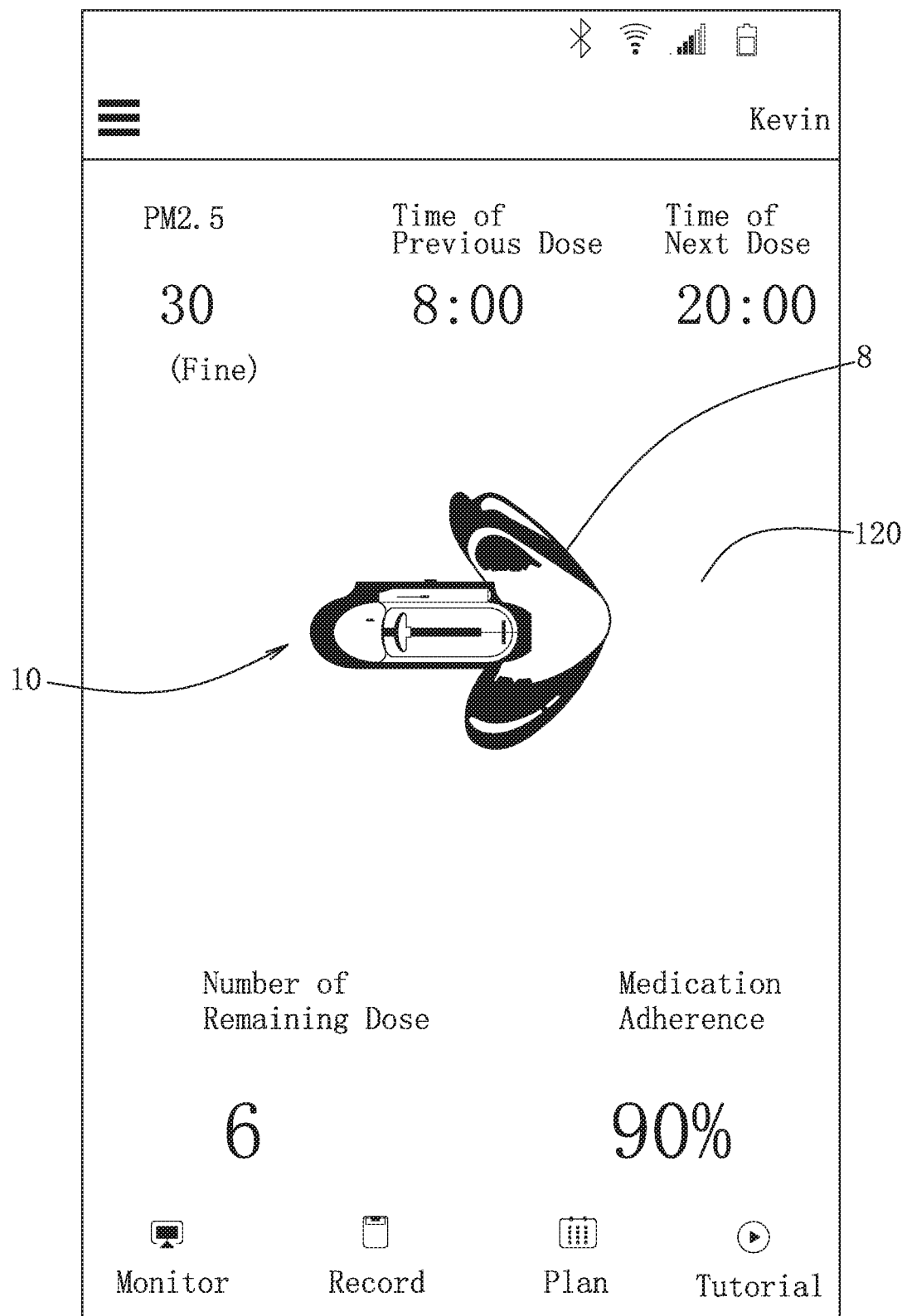

Referring to FIGS. 12 and 20, when the patient's lips approach the medication dispenser 10, the infrared proximity sensor 433, the capacitive sensor 432 and the infrared temperature sensor 434 in turn detect the presence of the patient's lips and generate the signals. The chip 415 determines that the patient is using the medication dispenser 10 upon reception of all of the signals generated by the capacitive sensor 432, the infrared proximity sensor 433 and the infrared temperature sensor 434. At this time, the animation display area 120 displays an image or a video of the mouth inhaling air in the medication dispenser 10, so as to remind the patient to begin to inhale.

In one embodiment, the chip 415 transfers the signals generated by the capacitive sensor 432, the infrared proximity sensor 433 or the infrared temperature sensor 434 to the portable mobile communication device 12 upon reception of each of the signals, and the portable mobile communication device 12 determines if the patient is using the medication dispenser 10 according to the signals generated by the capacitive sensor 432, the infrared proximity sensor 433 and the infrared temperature sensor 434.

Referring to FIGS. 6 and 10, during the inhalation of the patient, ambient air is drawn into the communicating channel 214 via the intake channels 213. Then, the air flows into the capsule 313 that is aligned with the mouthpiece 23 via the inlet path 215 to entrain the dose, and flows out of the mouthpiece 23 via the outlet path 217. The pressure sensor 419 detects the pressure difference in the communicating channel 214 during the inhalation of the patient, and sends a signal to the chip 415. The chip 415 then determines whether the flow rate of the inhalation of the patient is sufficient to deliver the dose according to the signal sent from the pressure sensor 419 using the abovementioned Hagen-Poiseuille law.

Figure 21:
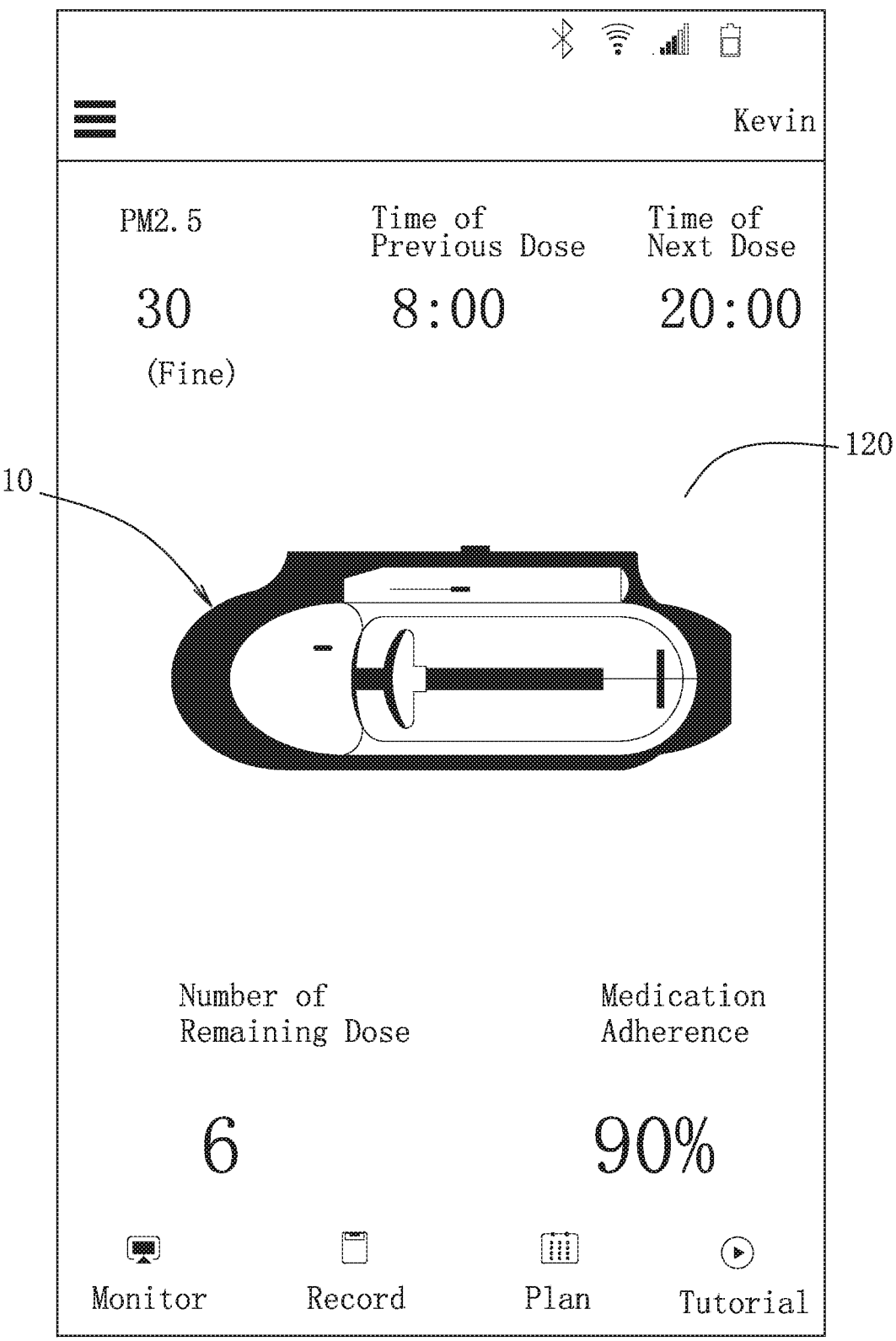

Referring to FIG. 21, after the inhalation is completed, the animation display area 120 displays an animation to remind the patient to move the outer casing 7 back to the close position. Referring further to FIGS. 5 and 15, the lever portion 351 of the operating member 35 is first driven to move to its original position. Then, the base seat 2 is rotated in the first rotational direction (R1, see FIG. 15) relative to the outer casing 7 until the outer casing 7 is moved to the close position (see FIG. 2). During the movement of the outer casing 7 from the open position to the close position, the protruding portion 742 of the slide block 74 is first separated from the push arm 426 of the second switch 425, and then actuates the push arm 426 of the first switch 424, so electric power is stopped being supplied to the first circuit board 411 from the battery 416, and the medication dispenser 10 is switched into the idle/standby state. When the first end 731 of the side plate 73 of the outer casing 7 abuts against the first flange 227 of the thumb hold portion 226 of the seat body 21, the outer casing 7 is moved to the close position (see FIG. 2).

Figure 22:
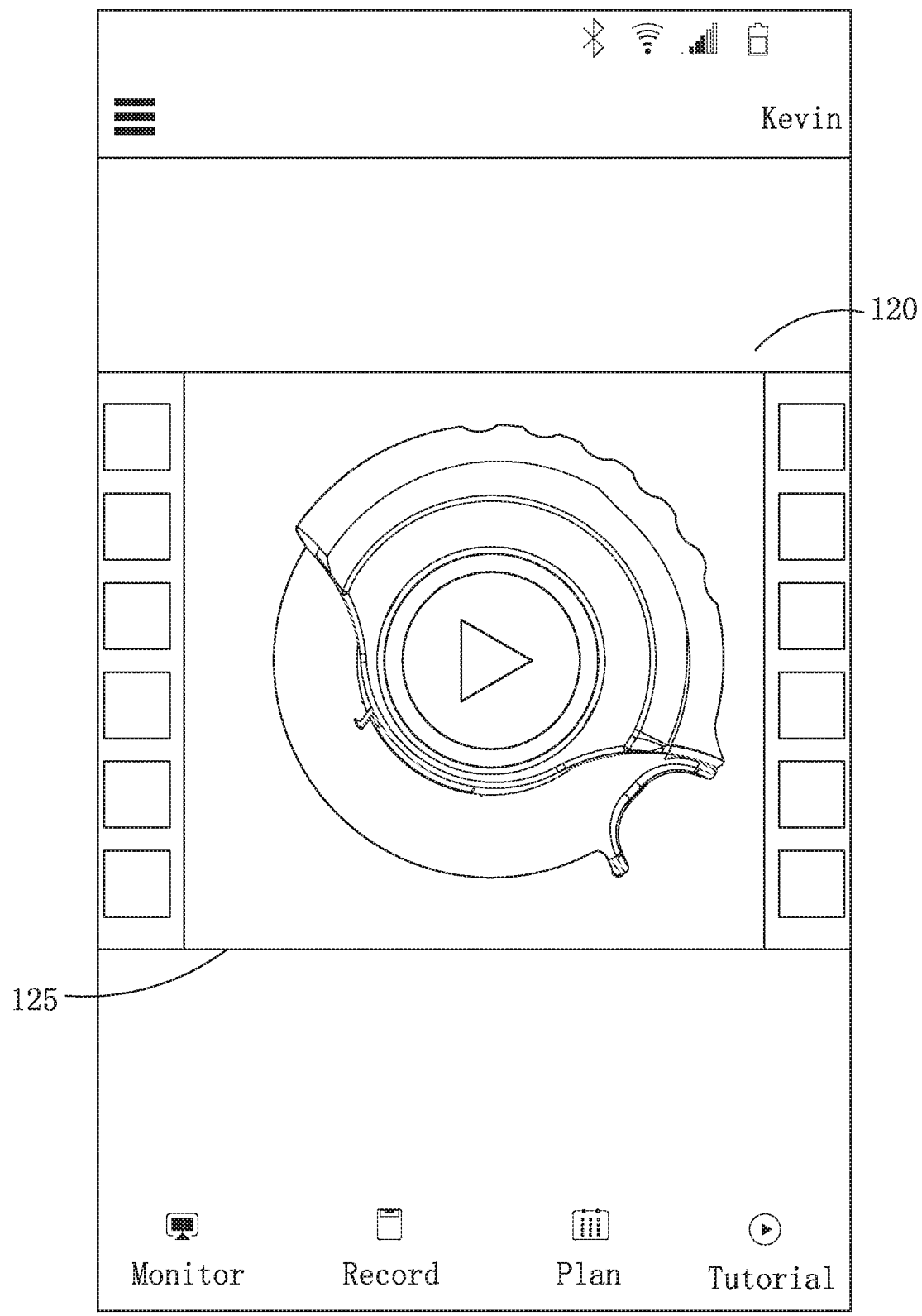

Referring to FIG. 22, the animation display area 120 may display a tutorial video 125 to demonstrate the operation of the medication dispenser 10 for a beginner.

Referring to FIGS. 1 and 2, in one embodiment, the location of the medication dispenser 10 can be reported by a Globe Positioning System (GPS) of the portable mobile communication device 12, so the medication dispenser 10 is prevented from being lost. Moreover, the portable mobile communication device 12 may transfer the locational data detected by the GPS to the network computer 14, and the network computer 14 gets environmental information, such as Air Pollution Index about the concentration of particle matter or carbon dioxide, from an environmental information center according to the locational data. The portable mobile communication device 12 receives the environmental information, and the application installed therein determines and reminds the patient whether it is suitable to use the medication dispenser 10.

In addition, the medication dispenser 10 may have built-in information of serial number or validity period that are registered in the network computer 14. The serial number enables the certification of the medication dispenser 10 before use, so as to prevent counterfeits. According to the register of the validity period, the medication dispenser 10 can be monitored by the application in the portable mobile communication device 12 to prevent the use after expiration thereof.

The network computer 14 may provide predetermined medication treatments to physicians or pharmacists, and the physicians or the pharmacists can monitor the status of a selected medication treatment of the patient by the monitoring device 15 connected to the network computer 14 so as to monitor medication adherence of the patient. The physicians and the pharmacists may be informed of the number of the remaining doses in the medication dispenser 10 via the monitoring device 15, so as to advise the patient when to reload the medication dispenser 10 via the network computer 14 and the portable mobile communication device 12.

Referring to FIG. 23, the second embodiment of the medication dispenser 10 (see FIG. 3) according to the disclosure is similar to the first embodiment, and is different from the first embodiment in the communication sub-unit 435.

In this embodiment, the seat body 21 is made of plastic, the communication sub-unit 435 is configured as a circuit pattern that is directly formed on the main wall portion 211 of the seat body 21 by Laser Selective Plating (LSP). The seat body 21 is first soaked in a water-soluble reactive metal solution, so an active metal layer (i.e., a catalyst metal layer or a seed layer) is formed on the main wall portion 211 of the seat body 21 before the seat body 21 is removed from the solution. Then, the active metal layer is etched by a process of laser etching to form a pattern, and a chemical-plating metal layer is formed on the patterned active metal layer by a process of chemical plating. Afterward, an electroplating metal layer is selectively formed on the chemical-plating metal layer by a process of electroplating. As such, the circuit pattern is formed on the main wall portion 211 of the seat body 21. The communication sub-unit 435 has two opposite ends respectively and electrically coupled to the first circuit board 411 and the second circuit board 431. It should be noted that the abovementioned Laser Selective Plating is just one of various processes for forming a Molded Interconnect Device (MID), and that any process for forming a circuit pattern on a non-metal substrate may be adopted to form the communication sub-unit 435 of the second embodiment.

Figure 24:
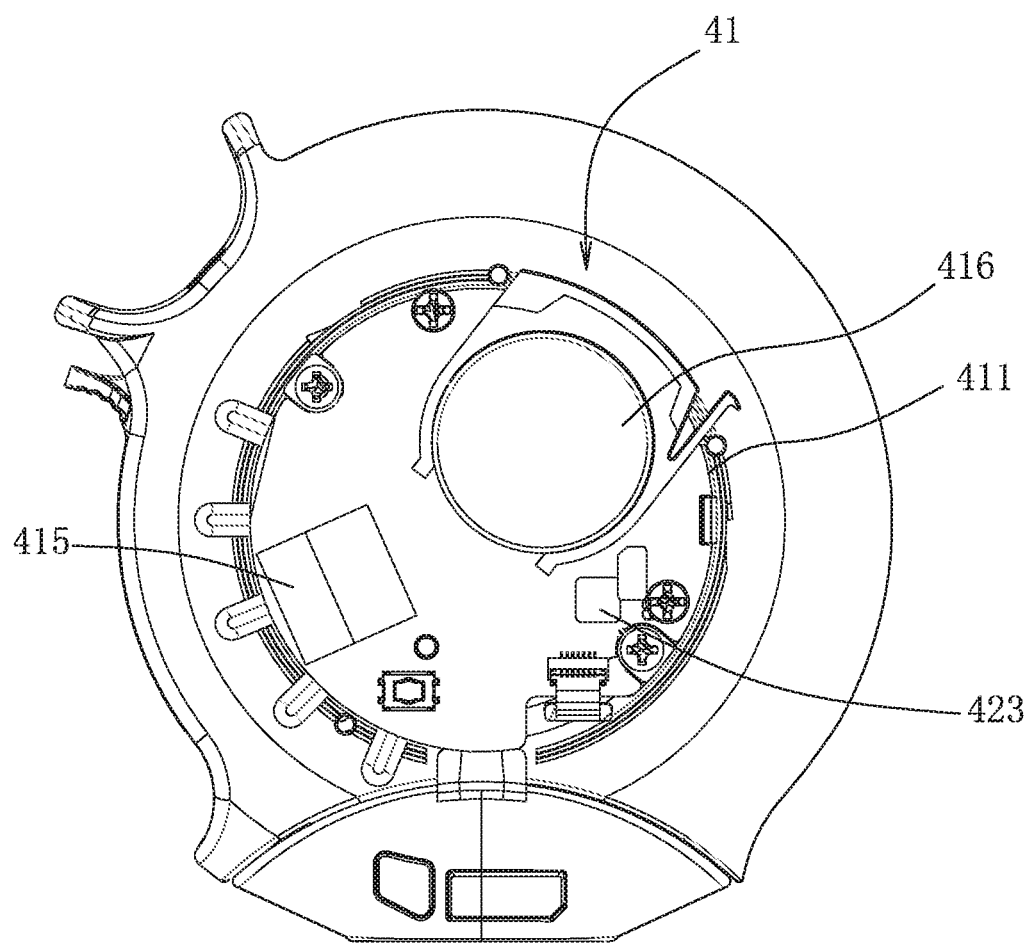
FIG. 24 is a schematic top view illustrating a modification of the medication dispenser of FIG. 3.

Referring to FIG. 24, a modification of the medication dispenser is different from the medication dispenser 10 (see FIG. 3) according to the disclosure in that the first and second switches 424, 425 of the first embodiment (see FIG. 5) are omitted, so the electric power is kept supplying from the battery 416 to the first circuit board 411. By such, the environmental sensor 423 continuously detects and records the humidity and temperature during use, load or transport of the medication dispenser 10 for a long term.

Figure 25:
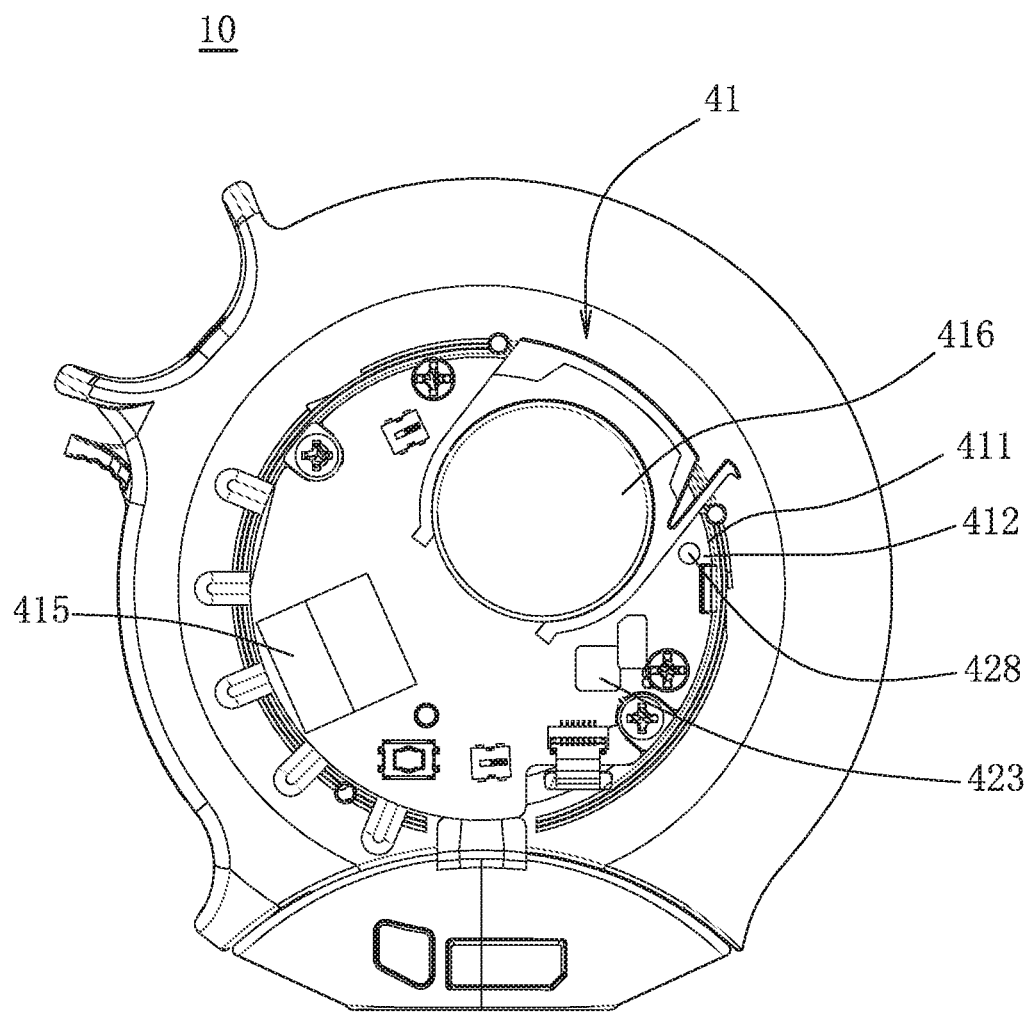
FIG. 25 is a schematic top view illustrating a third embodiment of the medication dispenser according to the disclosure.

Referring to FIG. 25, the third embodiment of the medication dispenser 10 according to the disclosure is similar to the first embodiment, and is different from the first embodiment in the main circuit module 41.

The main circuit module 41 further includes an auxiliary battery 428 that is disposed on the top surface 412 of the first circuit board 411. The auxiliary battery 418 is for supplying electrical power to the environmental sensor 423. By such, when the medication dispenser 10 is in the idle/standby state, electric power is kept supplying from the auxiliary battery 428 to the environmental sensor 423, so the environmental sensor 423 continuously detects and records the humidity and temperature for a long term.

Figure 26:
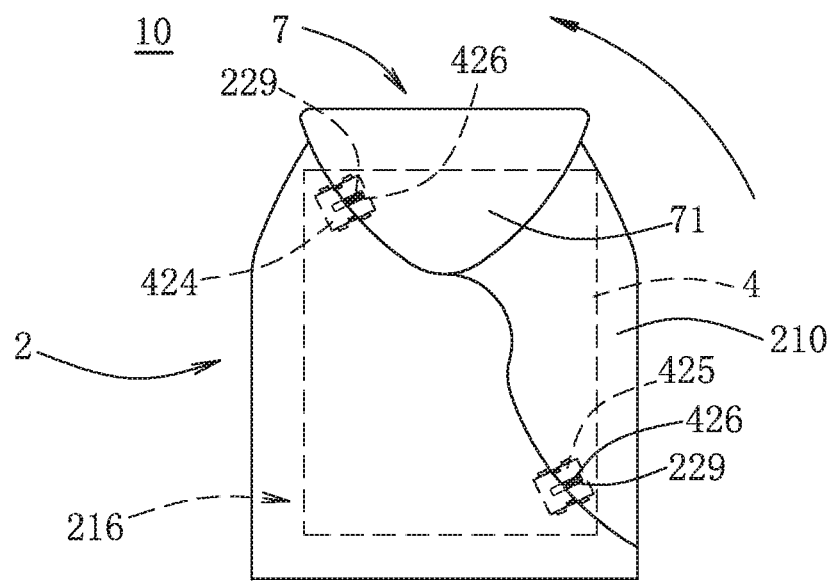
FIG. 26 is a schematic top view illustrating a fourth embodiment of the medication dispenser according to the disclosure in an idle/standby state.
Figure 27:
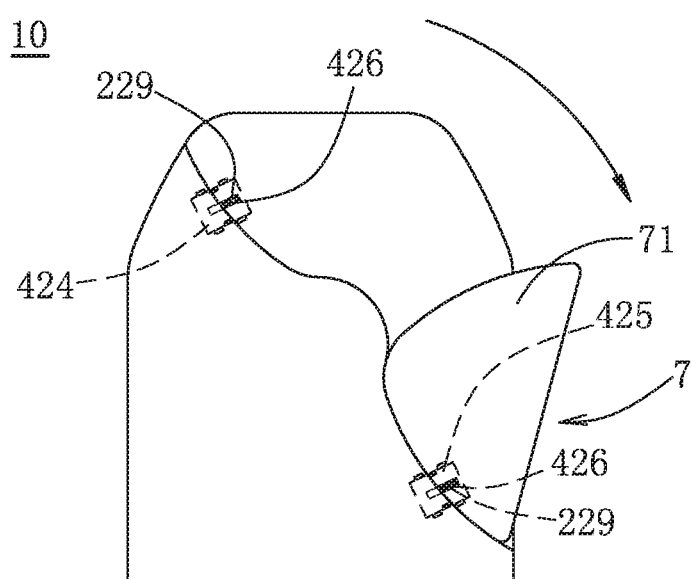
FIG. 27 is another schematic top view illustrating the fourth embodiment in an operating state.

Referring to FIGS. 26 and 27, the fourth embodiment of the medication dispenser 10 according to the disclosure is different from the first embodiment in the shape of the base seat 2 and the outer casing 7.

The base seat 2 of the fourth embodiment is substantially elliptical. The mechanism of the dispensing device (not shown) and the outer cover 7 can be referred to a medical inhaler of GlaxoSmithKline (GSK) named Arnuity Ellipta. The circuitry unit 4 is disposed in the retaining space 216 of the base seat 2. The top wall 210 of the base seat 2 is formed with two communication holes 229 that are in spatial communication with the retaining space 216. The push arm 426 of each of the first and second switches 424, 425 extends through the top wall 210 via a respective one of the communication holes 229. When the outer casing 7 is at a close position (see FIG. 26), the push arm 426 of the first switch 424 is actuated by the upper plate 71 of the outer casing 7, and the medication dispenser 10 is switched into the idle/standby state. When the outer casing 7 is at an open position (see FIG. 27), the push arm 426 of the second switch 425 is actuated by the upper plate 71 of the outer casing 7, and the medication dispenser 10 is switched into the operating state.

In summary, by virtue of the first and second switches 424, 425, the medication dispenser 10 is switched between the idle/standby state and the operating state upon the movement of the outer casing 7 between the close position and the open position.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A medication dispenser comprising
    a base seat;
    a notched wheel rotatable within said base seat; and
    a circuitry unit,
    wherein the notched wheel having an end surface and being formed with a plurality of equidistantly and angularly spaced-apart notches, each of said notches being adapted for receiving one of capsules of a conveying strip,
    wherein the circuitry unit being disposed on the base seat, and including a first circuit board, a plurality of magnets and a Hall sensor, the first circuit board having a surface facing toward the end surface of the notched wheel, the number of the magnets being determined upon the number of the notches of the notched wheel, the magnets being fixedly mounted to the end surface of the notched wheel, and being equidistantly and angularly spaced apart from each other, the Hall sensor being disposed on the surface of the first circuit board,
    wherein when the notched wheel is at a position where the Hall sensor is not registered with any one of the magnets, the Hall sensor being in a first detecting state in which no magnet is detected,
    wherein when the notched wheel is rotated to another position where the Hall sensor is registered with one of the magnets, said Hall sensor being in a second detecting state in which the magnet is detected,
    wherein the Hall sensor generating a signal upon switching from the first detecting state to the second detecting state or from the second detecting state to the first detecting state,
    wherein the number of said notches of said notched wheel is even, the number of said magnets being even, and
    wherein the number of said magnets is half the number of said notches, only one of any two adjacent ones of said notches being radially aligned with a corresponding one of said magnets with respect to a center of said notched wheel.

2. The medication dispenser as claimed in claim 1, wherein dose in a corresponding one of the capsules is determined to be inhaled when the Hall sensor is switched from the first detecting state to the second detecting state or from the second detecting state to the first detecting state.

3. The medication dispenser as claimed in claim 1, wherein the notched wheel has a top surface serving as the end surface, the first circuit board having a bottom surface serving as the surface, the base seat including a seat body, the seat body having a top wall, the top wall being formed with a mount hole, the Hall sensor being located within the mount hole, and being located above and spaced part from the top surface of the notched wheel.

4. The medication dispenser as claimed in claim 1, wherein the circuitry unit further includes:
a chip,
wherein when the chip receives the signal generated by the Hall sensor, the chip recording that the signal generated by the Hall sensor is received once, so as to determine dose in a corresponding one of the capsules is inhaled and to determine a decrement of number of remaining doses in the medication dispenser by one.

5. The medication dispenser as claimed in claim 1, wherein the base seat further includes a mouthpiece, and a seat body that is connected to the mouthpiece, the circuitry unit further including a lip detection module, the lip detection module including a capacitive sensor, an infrared proximity sensor and an infrared temperature sensor, and wherein during an approaching movement between the mouthpiece and a user's lips toward each other, the infrared proximity sensor, the capacitive sensor and the infrared temperature sensor in turn detecting a presence of the user's lips, the mouthpiece and the user's lips being determined to be in contact with each other when all of the infrared proximity sensor, the capacitive sensor and the infrared temperature sensor detect presence of the user's lips.

6. The medication dispenser as claimed in claim 1, wherein the medication dispenser further includes:
an outer casing, the base seat including a mouthpiece, the circuitry unit further including a battery, a first switch that is disposed on the first circuit board, and a second switch that is disposed on the first circuit board,
wherein the outer casing being movably mounted to the base seat, and movable relative to the base seat between a close position where the outer casing covers the mouthpiece, and an open position where the outer casing uncovers the mouthpiece,
wherein when the outer casing is at the close position, the first switch being actuated such that electric power is prevented from being supplied from said battery to the first circuit board, and
wherein when the outer casing is at the open position, the second switch being actuated such that electric power is supplied from the battery to the first circuit board.

7. The medication dispenser as claimed in claim 6, wherein the base seat further includes:
a seat body that has a top wall, the first circuit board being mounted to the top wall and having a top surface, the first switch and the second switch being disposed on the top surface of the first circuit board, and being contactable with the outer casing.

8. The medication dispenser as claimed in claim 7, further comprising:
a cover unit that covers the first circuit board, and that includes a cover plate, the cover plate having an arc-shaped guide groove that is formed in a top surface of the cover plate, and two communication holes that are formed in a bottom surface of the cover plate and that are respectively in spatial communication with two opposite ends of the guide groove, each of the first switch and the second switch including a push arm, the push arm of each of the first and second switches extending into the guide groove via a respective one of the communication holes, the outer casing partially extending into the guide groove of the cover plate for contact with the push arm of the first switch or with the push arm of the second switch.

9. The medication dispenser as claimed in claim 1, wherein the base seat includes a mouthpiece, the base seat including a top wall, and defines a flow path located between the top wall and the mouthpiece, said circuitry unit further including a pressure sensor that is located in the flow path for detecting pressure difference in the flow path, the medication dispenser further comprising a dispensing device that is disposed in the base seat and that includes a conveying strip, the conveying strip including a capsule that is in fluid communication with the flow path and that is located downstream of the pressure sensor.

10. The medication dispenser as claimed in claim 9, wherein the base seat further includes:
a seat body that is connected to the mouthpiece, the seat body having the top wall, the top wall being formed with a plurality of spaced-apart intake channels, and an arc-shaped communicating channel that is in fluid communication with the intake channels, the seat body defining a retaining space that is for retaining the dispensing device, an inlet path that is in fluid communication with an end of the communicating channel and the retaining space, the first circuit board being fixedly mounted to the top wall, and having a bottom surface, a portion of the bottom surface of the first circuit board corresponding in position to the communicating channel and being located above the communicating channel, the pressure sensor being disposed on the bottom surface of the first circuit board, and being located adjacent to a end portion of the communicating channel proximate to the inlet path.

11. A medication dispenser comprising
a base seat;
a notched wheel that is rotatable within the base seat;
a Hall sensor that is fixedly disposed; and
a plurality of magnets,
wherein the notched wheel being formed with a plurality of equidistantly and angularly spaced-apart notches, each of the notches being adapted for receiving one of capsules of a conveying strip, the notched wheel having two opposite ends along a rotating axis thereof, and two end surfaces respectively at the opposite ends, said magnets being fixedly mounted to one of the end surfaces that is proximate to said Hall sensor, and being spaced apart from each other, during rotation of the notched wheel, the magnets being driven to be proximate to or distal from the Hall sensor so as to switch the Hall sensor between a first detecting state and a second detecting state,
wherein the number of said notches of said notched wheel is even, the number of said magnets being even, and
wherein the number of said magnets is half the number of said notches, only one of any two adjacent ones of said notches being radially aligned with a corresponding one of said magnets with respect to a center of said notched wheel.

12. The medication dispenser as claimed in claim 11, wherein said notched wheel has a top surface serving as said end surface, said first circuit board having a bottom surface serving as said surface, said base seat including a seat body, said seat body having a top wall, said top wall being formed with a mount hole, said Hall sensor being located within said mount hole, and being located above and spaced part from said top surface of said notched wheel.

13. The medication dispenser as claimed in claim 11, wherein said circuitry unit further includes a chip, said Hall sensor generating a signal upon switch from the first detecting state to the second detecting state or from the second detecting state to the first detecting state, when said chip receives the signal generated by the Hall sensor, said chip recording that the signal generated by the Hall sensor is received once, so as to determine dose in a corresponding one of the capsules is inhaled and to determine a decrement of number of remaining doses in said medication dispenser by one.

14. The medication dispenser as claimed in claim 11, wherein said medication dispenser further includes an outer casing, said base seat including a mouthpiece, said circuitry unit further including a battery, a first switch that is disposed on said first circuit board, and a second switch that is disposed on said first circuit board, said outer casing being movably mounted to said base seat, and movable relative to said base seat between a close position where said outer casing covers said mouthpiece, and an open position where said outer casing uncovers said mouthpiece, when said outer casing is at the close position, said first switch being actuated such that electric power is prevented from being supplied from said battery to said first circuit board, when said outer casing is at the open position, said second switch being actuated such that electric power is supplied from said battery to said first circuit board.

15. A medication dispenser comprising
a base seat;
a notched wheel rotatable within the base seat;
a circuit board fixedly disposed in the base seat;
a Hall sensor fixedly disposed on a surface of the circuit board that faces toward the notched wheel; and
a plurality of magnets, the notched wheel being formed with a plurality of spaced-apart notches, each of the notches being adapted for receiving one of capsules of a conveying strip, the magnets being co-rotatably mounted to the notched wheel, and being spaced apart from each other, during rotation of the magnets, the Hall sensor being switched between different detecting states in response to movement of the magnets toward and away from the Hall sensor,
wherein the number of said notches of said notched wheel is even, the number of said magnets being even, and
wherein the number of said magnets is half the number of said notches, only one of any two adjacent ones of said notches being radially aligned with a corresponding one of said magnets with respect to a center of said notched wheel.

16. The medication dispenser as claimed in claim 15, wherein said notched wheel has a top surface serving as said end surface, said first circuit board having a bottom surface serving as said surface, said base seat including a seat body, said seat body having a top wall, said top wall being formed with a mount hole, said Hall sensor being located within said mount hole, and being located above and spaced part from said top surface of said notched wheel.

17. The medication dispenser as claimed in claim 15, wherein said circuitry unit further includes a chip, said Hall sensor generating a signal upon switch from one of the detecting states to another one of the detecting states, when said chip receives the signal generated by the Hall sensor, said chip recording that the signal generated by the Hall sensor is received once, so as to determine dose in a corresponding one of the capsules is inhaled and to determine a decrement of number of remaining doses in said medication dispenser by one.

18. The medication dispenser as claimed in claim 15, wherein said medication dispenser further includes an outer casing, said base seat including a mouthpiece, said circuitry unit further including a battery, a first switch that is disposed on said first circuit board, and a second switch that is disposed on said first circuit board, said outer casing being movably mounted to said base seat, and movable relative to said base seat between a close position where said outer casing covers said mouthpiece, and an open position where said outer casing uncovers said mouthpiece, when said outer casing is at the close position, said first switch being actuated such that electric power is prevented from being supplied from said battery to said first circuit board, when said outer casing is at the open position, said second switch being actuated such that electric power is supplied from said battery to said first circuit board.

\* \* \* \* \*